US012636379B2

(12) United States Patent
Callan et al.

(10) Patent No.: US 12,636,379 B2
(45) **Date of Patent: *May 26, 2026**

(54) MICROBUBBLE-CHEMOTHERAPEUTIC AGENT COMPLEX FOR SONODYNAMIC THERAPY

(71) Applicant: UNIVERSITY OF ULSTER, Northern Ireland (GB)

(72) Inventors: John Callan, Newtownabbey (GB); Anthony McHale, Newtownabbey (GB); Eleanor Stride, Oxford (GB)

(73) Assignee: SONOTARG LIMITED, Belfast (GB)

(*) Notice: Subject to any disclaimer, the term of this patent is extended or adjusted under 35 U.S.C. 154(b) by 800 days.

This patent is subject to a terminal disclaimer.

(21) Appl. No.: 17/734,484

(22) Filed: May 2, 2022

(65) Prior Publication Data

US 2022/0347314 A1 Nov. 3, 2022

Related U.S. Application Data

(63) Continuation of application No. 15/777,831, filed as application No. PCT/GB2016/053682 on Nov. 23, 2016, now Pat. No. 11,382,987.

(30) Foreign Application Priority Data

Nov. 23, 2015 (GB) ..................................... 1520649

(51) Int. Cl.
*A61K 9/00* (2006.01)
*A61K 41/00* (2020.01)
(Continued)

(52) U.S. Cl.
CPC ...... *A61K 47/6925* (2017.08); *A61K 41/0033* (2013.01); *A61K 47/545* (2017.08);
(Continued)

(58) Field of Classification Search
CPC .................................................. A61K 47/6925
See application file for complete search history.

(56) References Cited

U.S. PATENT DOCUMENTS

| | | | |
|---|---|---|---|
| 9,040,721 | B2 | 5/2015 | Jones et al. |
| 9,095,612 | B2 | 8/2015 | Jones et al. |

(Continued)

FOREIGN PATENT DOCUMENTS

| | | |
|---|---|---|
| EP | 2 253 308 | 11/2010 |
| RU | 2014 108 245 | 10/2015 |

(Continued)

OTHER PUBLICATIONS

Written Opinion issued Nov. 21, 2023 in corresponding Singapore Application No. 11201804312R.

(Continued)

*Primary Examiner* — Paul W Dickinson
(74) *Attorney, Agent, or Firm* — Wenderoth, Lind & Ponack, L.L.P.

(57) ABSTRACT

The invention relates to methods of sonodynamic therapy comprising the co-administration of a microbubble-chemotherapeutic agent complex together with a microbubble-sonosensitiser complex. It further relates to pharmaceutical compositions comprising these complexes and their use in methods of sonodynamic therapy and/or sonodynamic diagnosis. Such methods find particular use in the treatment of cancer, e.g. pancreatic cancer.

17 Claims, 14 Drawing Sheets

Specification includes a Sequence Listing.

(51) Int. Cl.
*A61K 47/54* (2017.01)
*A61K 47/69* (2017.01)
*A61P 35/00* (2006.01)

(52) U.S. Cl.
CPC ............ *A61K 47/557* (2017.08); *A61P 35/00* (2018.01); *A61K 2121/00* (2013.01)

(56) References Cited

U.S. PATENT DOCUMENTS

| | | | |
|---|---|---|---|
| 2003/0044354 | A1 | 3/2003 | Carpenter, Jr. et al. |
| 2009/0087384 | A1 | 4/2009 | Erguen et al. |
| 2013/0072854 | A1 | 3/2013 | Mohan |
| 2013/0231604 | A1 | 9/2013 | Jones et al. |

FOREIGN PATENT DOCUMENTS

| | | |
|---|---|---|
| WO | 2006/127953 | 11/2006 |
| WO | 2009/055720 | 4/2009 |
| WO | 2012/143739 | 10/2012 |
| WO | 2013/041500 | 3/2013 |
| WO | 2013/052776 | 4/2013 |
| WO | 2015/038882 | 3/2015 |
| WO | 2015/141917 | 9/2015 |

OTHER PUBLICATIONS

Costley D. et al., "Treating cancer with sonodynamic therapy: A review", International Journal of Hyperthermia, Jan. 13, 2015, vol. 31, No. 2, pp. 107-117.

International Search Report and Written Opinion of the International Searching Authority, issued Mar. 9, 2017 in corresponding International Application No. PCT/GB2016/053682.

McEwan et al., "Oxygen carrying microbubbles for enhanced sonodynamic therapy of hypoxic tumours", Journal of Controlled Release, 203(4): 51-56 (2015).

Koevary, "Selective toxicity of rose engal to ovarian cancer cells in vitro", Int J. Physiol Pathophysiol Pharacol, 4(2): 99-107 (2012).

Deng et al., "Reversal of multidrug resistance phenotype in human breast cancer cells using doxorubicin-liposome-microbubble complexes assisted by ultrasound", Journal of Controlled Release, 174(25): 109-116 (2013).

Tinkov et al., "New doxorubicin-loaded phospholipid microbubbles for targeted tumor therapy: Part 1—Formulation development and in-vitro characterization", Journal of Controlled Release, 143(1): 143-150 (2010).

Yu et al., "Anticancer Potency of Cytotoxic Drugs after Exposure to High-Intensity Focused Ultrasound in the Presence of Microbubbles and Hematoporphyrin", Molecular Pharmaceutics, 8(4): 1408-1415 (2011).

McEwan et al., "Combined sonodynamic and antimetabolite therapy for the improved treatment of pancreatic cancer using oxygen loaded microbubbles as a delivery vehicle", Biomaterials, 80(1): 20-32 (2016).

International Preliminary Report on Patentability issued Jun. 7, 2018 in International (PCT) Application No. PCT/GB2016/053682.

Search Report issued Sep. 2, 2016 in British Application No. GB1520649.3.

Lentacker, I., et al., "Design and Evaluation of Doxorubicin-containing Microbubble for Ultrasound-triggered Doxorubicin Delivery: Cytotoxicity and Mechanisms Involved", Molecular Therapy, pp. 101-108 (Year: 2010).

Translation of Office Action issued Mar. 4, 2020 in corresponding Russian Application No. 2018121275/04.

Wu, Y., et al., "Preparation and antitumor activity of bFGFmediated active targeting doxorubicin microbubbles", Drug Dev. Ind. Pharm., pp. 1712-1719 (Year: 2013).

Liang, L., et al., "The Combined Effects of Hematoporphyrin Monomethylether-SDT and Doxorubicin on the Proliferation of QBC939 Cell Lines", Ultrasoun in Med. Biol., pp. 146-160 (Year: 2013).

Nomikou, N., et al., "Microbubble-sonosensitiser conjugates as therapeutics in sonodynamic therapy", ChemComm, pp. 833-8334 (Year: 2012).

Yu, T., et al., "Sonochemotherapy Against Cancers", Nova Science Publishers, pp. 189-200 (Year: 2010).

Office Action issued Sep. 15, 2020 in corresponding Chinese Patent Application No. 201680074452.1, with English Translation.

Zheng et al., "Construction of targeted ultrasound microbubbles with anti P-selectin monoclone antibody via streptavidin bridge and evaluation of its reliability using fluorescence in vitro", Chin J Med Imaging Technol, 2008, vol. 24, No. 8, pp. 1182-1185.

Wang et al., "Research progress of ultrasound targeted destruction of microbubbles in tumor treatment", Chinese Journal of Medical Imaging, 2013, pp. 866-868 and 873.

Soininen et al., "Targeted delivery via avidin fusion protein: Intracellular fate of biotinylated doxorubicin derivative and cellular uptake kinetics and biodistribution of biotinylated liposomes", European Journal of Pharmaceutical Sciences, 2012, vol. 47, pp. 848-856.

Gao et al., "Adriamycin enhances the sonodynamic effect of chlorin e6 against the proliferation of human breast cancer MDA-MB-231 cells in vitro", J South Med Univ, 2010, vol. 30, No. 10, pp. 2291-2294.

Feng et al., "Preparation and Pharmacodynamic Evaluation of Biotinylated Resveratrol", Nat Prod Res Dev, 2009, vol. 21, pp. 988-991.

Office Action issued May 7, 2021 in corresponding Chinese Patent Application No. 201680074452.1, with English Translation.

Luo Rongcheng et al., "New Progress in Comprehensive Diagnosis and Treatment of Tumors", People's Military Medical Publishing House, Aug. 31, 2000, 3rd Edition, paragraph 3 of the left column on p. 103.

Office Action issued Sep. 23, 2021 in corresponding Russian Patent Application No. 2018121275/04(033506), with English Translation.

Small Medical Encyclopedia, edited by Pokrovsky, Moscow, "Medicine", 1996, p. 90.

Popular Medical Encyclopedia, chief editor V.I., 1997, p .317 (medicines).

Wang, X. et al., "Combination of Protoporphyrin IX-Mediated Sonodynamic Treatment With Doxorubicin Synergistically Induced Apoptotic Cell Death of a Multidrug-Resistant Leukemia K562/DOX Cell Line", Ultrasound in Med & Biol., 2015, vol. 41, No. 10, pp. 2731-2739.

Yan et al., "Paclitaxel-liposome-microbubble complexes as ultrasound-triggered therapeutic drug delivery carriers", Journal of Controlled Release, 2013, vol. 166, pp. 246-255.

RB

RB1-COOH

RB-COOH (a)

(b)

(a)

(b)

(b)

(c)

MB-9

MICROBUBBLE-CHEMOTHERAPEUTIC AGENT COMPLEX FOR SONODYNAMIC THERAPY

SEQUENCE LISTING

A sequence listing in electronic (ASCII text file) format is filed with this application and incorporated herein by reference. The name of the ASCII text file is "Sequence_listing_0830.txt"; the file was created on Nov. 20, 2025; the size of the file is 1,377 bytes.

TECHNICAL FIELD

The present invention relates to improvements in and relating to methods of sonodynamic therapy and, in particular, to the treatment of diseases characterised by hyperproliferative and/or abnormal cells. More specifically, the invention relates to the targeted treatment of deep-sited tumours using a combined sonodynamic and anti-cancer therapy.

The invention further relates to certain novel sensitising agents, to methods for their preparation and to their use as sensitisers in methods of photodynamic therapy (PDT) and/or sonodynamic therapy (SDT). It also relates to the use of some of these agents as near-infrared (NIR) imaging agents and their use in diagnostic imaging methods.

BACKGROUND OF THE INVENTION

Conventional treatment of deeply-sited tumors typically involves major surgery, chemotherapy, radiotherapy or combinations of all of these. All three interventions may result in various complications including sepsis. Therefore, the development of more targeted and less invasive therapeutic approaches with improved efficacy to treat such patients is highly sought after. Pancreatic cancer is one example of a deep-sited tumor. It remains one of the most lethal types of cancer known with less than 20% of those diagnosed being eligible for curative surgical treatment. It accounts for approximately 2% of all cancers with a five year survival of 15-21% in patients who have a surgical resection followed by systemic chemotherapy.

Methods known for use in the treatment of cancer include photodynamic therapy (PDT). PDT involves the application of photosensitising agents to the affected area, followed by exposure to photoactivating light to convert these into cytotoxic form. This results in the destruction of cells and surrounding vasculature in a target tissue. Photosensitisers which are currently approved for use in PDT absorb light in the visible region (below 700 nm). However, light of this wavelength has limited ability to penetrate the skin; this penetrates to a surface depth of only a few mm. Whilst PDT may be used to treat deeper sited target cells, this generally involves the use of a device, such as a catheter-directed fibre optic, for activation of the photosensitiser. Not only is this a complicated procedure, but it precludes access to certain areas of the body. It also compromises the non-invasive nature of the treatment. Thus, although appropriate for treating superficial tumours, the use of PDT in treating deeply seated cells, such as tumour masses, and anatomically less accessible lesions is limited.

Sonodynamic therapy (SDT) is a more recent concept and involves the combination of ultrasound and a sonosensitising drug (also referred to herein as a "sonosensitiser"). In a manner similar to PDT, activation of the sonosensitiser by acoustic energy results in the generation of reactive oxygen species (ROS), such as singlet oxygen, at the target site of interest. Such species are cytotoxic, thereby killing the target cells or at least diminishing their proliferative potential. Many known photosensitising agents can be activated by acoustic energy and are thus suitable for use in SDT. Since ultrasound readily propagates through several cm of tissue, SDT provides a means by which tumours which are located deep within the tissues may be treated. As with light, ultrasound energy can also be focused on a tumour mass in order to activate the sonosenitiser thereby restricting its effects to the target site.

SDT offers some significant advantages over PDT: ultrasound is widely accepted as a cost effective and safe clinical imaging modality and, unlike light, can be tightly focused with penetration in soft tissue up to several tens of centimetres depending on the ultrasound frequency used.

In WO 2012/143739 sonosensitisers are conjugated to a gas-filled microbubble (MB) to provide a microbubble-sonosensitiser "complex" for use in SDT. These complexes permit effective delivery of the active sonosensitiser in a site-specific manner by a controlled destruction of the bubble using ultrasound. Subsequent or simultaneous sono-activation of the targeted sonosensitiser results in cell destruction at the target site and regression of tumor tissues. The use of a microbubble also leads to a reduction in toxic side-effects due to the shielding of the sonosensitiser from potential light activation prior to reaching the desired target site.

Recently, the inventors have demonstrated the effectiveness of SDT using microbubble-sonosensitiser complexes for the treatment of pancreatic cancer in a pre-clinical model (McEwan et al. J Control Release. 2015; 203, 51-6). These studies have shown that an injection of ultrasound-responsive microbubbles (MB), filled with gaseous oxygen and bearing a Rose Bengal sensitiser, provides a statistically significant SDT-mediated reduction in tumour growth in mice bearing human xenograft BxPC-3 tumours when compared to tumours treated with a similar MB conjugate comprising SF6 as the core gas. The rationale for the incorporation of oxygen in the core of the MB was to enhance the amount of ROS generated in the tumour microenvironment during the sonodynamic event, as oxygen is a substrate for ROS production in SDT. Pancreatic tumours, in particular, are known to be highly hypoxic and this further negatively impacts the efficacy of approaches such as PDT/SDT that depend on oxygen for the generation of cytotoxic ROS.

It has also been demonstrated that combining the benchmark pancreatic cancer antimetabolite therapeutics 5-fluorouracil (5-FU) and gemcitabine with complimentary chemotherapies such as irinotecan and oxaliplatin can improve the mean survival rate for pancreatic cancer sufferers (Lee et al., Chemotherapy. 2013; 59, 273-9). However, this combination, known as FOLFIRINOX, results in significant side-effects and is only indicated for patients who are otherwise fit and healthy.

A need thus exists for alternative methods for the treatment of deep-sited, inaccessible tumors, such as pancreatic cancer, in particular methods which are non-invasive or minimally invasive and which are without adverse side-effects. Such methods would have obvious socio-economic benefits, e.g. in terms of reduced patient trauma, reduced treatment expense and reduced costs associated with any hospital stay. The present invention addresses this need.

SUMMARY OF THE INVENTION

The inventors now propose that as anti-metabolite therapy and SDT exert their cytotoxic effects via different mechanisms (the former through thymidylate synthase inhibition and the latter through oxidation of cellular substrates) their combination in a single therapeutic regime may provide significant patient benefit.

Specifically, the inventors have now found that the use of microbubbles to deliver both a sonosensitiser and an anti-metabolite confers a number of advantages when used in methods of sonodynamic therapy. Specifically, what they have found is that the delivery of both the sonosensitiser and anti-metabolite in the form of a complex (or complexes) with a microbubble permits effective delivery of both agents in a site-specific manner (e.g. to an internal tumour) by a controlled destruction of the bubbles using ultrasound. Sono-activation of the targeted sonosensitiser results in the generation of ROS which destroy tumor cells at the target site. This action is complimented by the action of the anti-metabolite which exerts its cytotoxic effect directly at the intended target site. By using the microbubble as a carrier for both agents, non-specific uptake of these by non-target tissues is reduced, thus providing a significant advantage over systemic delivery. This therapy is thus expected to reduce side-effects and, in turn, provide significant patient benefit.

Furthermore, by utilising an oxygen-loaded MB platform in combination with externally applied ultrasound to deliver not only oxygen, but also the anti-metabolite and sensitiser to the tumour microenvironment, the inventors propose that a highly targeted therapy can be realised, particularly as a result of increasing the therapeutic indices of the sensitiser and the anti-metabolite chemotherapeutic drug. The ability of the microbubble to deliver oxygen to the tumor is expected to further enhance such therapies which are dependent on oxygen to mediate their therapeutic effects.

Described herein is the preparation of oxygen-loaded lipid-stabilised MBs ($O_2$MB) with either Rose Bengal ($O_2$MB-RB) or 5-FU ($O_2$MB-5FU) attached to their surface. The resulting conjugates are characterised in terms of MB stability and ultrasound-mediated oxygen release and demonstrate ultrasound-mediated cytotoxicity of combined anti-metabolite/SDT treatment in a panel of pancreatic cancer cell lines in vitro. Therapeutic efficacy of the combined approach is demonstrated using a preclinical ectopic human xenograft pancreatic tumour model in mice and compared with conventional therapeutic approaches exploiting 5-FU or gemcitabine treatment alone. Evidence is also provided to demonstrate that SDT has a significant impact on signal transduction processes that mediate the immune response and cell proliferation.

The results provided herein illustrate not only the potential of combined SDT/anti-metabolite therapy as a stand alone treatment option in pancreatic cancer, but also the capability of $O_2$-loaded MBs to deliver $O_2$ to the tumour microenvironment in order to enhance the efficacy of therapies that depend on $O_2$ to mediate their therapeutic effect. The use of MBs to facilitate delivery of $O_2$ as well as the sensitiser/anti-metabolite, combined with the possibility to activate the sensitiser using externally applied ultrasound, provides a more targeted approach with improved efficacy and reduced side-effects when compared with conventional systemic administration of anti-metabolite drugs alone.

This novel approach to the treatment of pancreatic cancer extends to the treatment of other diseases and conditions characterised by hyperproliferative and/or abnormal cells, in particular to the treatment of other deeply-sited tumors. As will be described herein, this approach therefore has broader application which extends to the treatment of other such diseases and conditions using other chemotherapeutic drugs.

DETAILED DESCRIPTION OF THE INVENTION

In its broadest aspect the invention provides a microbubble-chemotherapeutic agent complex for use in a method of sonodynamic therapy. As used herein, the term "sonodynamic therapy" is intended to refer to a method involving the combination of ultrasound and a sonosensitiser (also referred to herein as a "sonosensitising drug") in which activation of the sonosensitiser by acoustic energy results in the generation of reactive oxygen species, such as singlet oxygen.

The microbubble-chemotherapeutic agent complex comprises a microbubble attached to or otherwise associated with at least one chemotherapeutic agent. Where the microbubble is attached to more than one chemotherapeutic agent, these may be the same or different. Generally, however, the chemotherapeutic agents attached to a particular microbubble will be identical. To the extent that such a complex is intended for use in methods of SDT, it will be ultrasound-responsive. Specifically, it is intended that the microbubble component of the complex can be ruptured by application of ultrasound, thereby releasing the chemotherapeutic agent at the desired target site.

The chemotherapeutic agent (or agents) may be linked to the microbubble through covalent or non-covalent means, e.g. via electrostatic interaction, van der Waals forces and/or hydrogen bonding. In one embodiment the microbubble is electrostatically bound to the chemotherapeutic agent. In another embodiment it may be covalently bound, i.e. the chemotherapeutic agent will be attached to the microbubble by one or more covalent bonds.

Preferably, the interaction between the chemotherapeutic agent (or agents) and the microbubble will involve strong non-covalent bonding such as the biotin-avidin interaction. In this embodiment one component of the binding pair (e.g. the chemotherapeutic agent) is functionalised with biotin and the other (e.g. the microbubble) with avidin. Since avidin contains multiple binding sites for biotin, this will typically also be bound to the microbubble via a biotin-avidin interaction. For example, a microbubble may be functionalised with biotin to form a biotinylated microbubble which is then incubated with avidin. Once the avidin is bound to the bubble, this permits binding of any further biotinylated moieties, such as the chemotherapeutic agent. The resulting linkage between the microbubble and the chemotherapeutic agent may thus take the form a "biotin-avidin-biotin" interaction.

As used herein, the term "chemotherapeutic agent" is intended to broadly encompass any chemical or biological compound useful in the treatment of cancer. It includes growth inhibitory agents and other cytotoxic agents. The term "growth inhibitory agent" refers to a compound which inhibits growth of a cell, especially a cancer cell either in vitro or in vivo.

For use in the invention, suitable classes of chemotherapeutics and examples within those classes include the following: antifolates (e.g. methotrexate); 5-fluoropyrimidines (e.g. 5-fluorouracil or 5-FU); cytidine analogues (e.g. gemcitabine); purine antimetabolites (e.g. mercaptopurine); alkylating agents (e.g. cyclophosphamide); non-classical alkylating agents (e.g. dacarbazine); platinum analogues (e.g. cisplatin); antitumour antibiotics (e.g. actinomycin D, bleomycin, mitomycin C); bioreductive drugs (e.g. mitomycin C, Banoxantrone (AQ4N)); anthracyclines (e.g. doxorubicin, mitoxantrone); topoisomerase I inhibitors (e.g. irinotecan); topoisomease II inhibitors (e.g. etoposide);

antimicrotubule agents such as *vinca* alkaloids (e.g. vincristine), taxols (e.g. paclitaxel), and epothilones (e.g. ixabepiline); antioestrogens (e.g. tamoxifen); antiandrogens (e.g. biclutamide, cyproterone acetate); aromatase inhibitors (e.g. anastrazole, formestan); antiangiogenic or hypoxia targeting drugs (either naturally occuring, e.g. endostatin, or synthetic, e.g. gefitinib, lenalidomide); antivascular agents (e.g. cambretastatin);

tyrosine kinase inhibitors (e.g. gefitinib, erlotinib, vandetanim, sunitinib); oncogene or signalling pathway targeting agents (e.g. tipfarnib, lonafarnib, naltrindole, rampamycin); agents targeting stress proteins (e.g. geldanamycin and analogues thereof); autophagy targeting agents (e.g. chloroquine); proteasome targeting agents (e.g. bortezomib); telomerase inhibitors (targeted oligonucleotides or nucleotides); histone deacetylase inhibitors (e.g. trichostatin A, valproic acid); DNA methyl transferase inhibitors (e.g. decitabine); alkyl sulfonates (e.g. busulfan, improsulfan and piposulfan); aziridines (e.g. benzodopa, carboquone, meturedopa, and uredopa); ethylenimines and methylamelamines (e.g. altretamine, triethylenemelamine, trietylenephosphoramide, triethylenethiophosphaoramide and trimethylolomelamine); nitrogen mustards (e.g. chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard); nitrosureas (e.g. carmustine, chlorozotocin, fotemustine, lomustine, nimustine, ranimustine); purine analogues (e.g. fludarabine, 6-mercaptopurine, thiamiprine, thioguanine); pyrimidine analogues (e.g. ancitabine, azacitidine, 6-azauridine, carmofur, cytarabine, dideoxyuridine, doxifluridine, enocitabine, floxuridine); androgens (e.g. calusterone, dromostanolone propionate, epitiostanol, mepitiostane, testolactone); and anti-adrenals (e.g. aminoglutethimide, mitotane, trilostane). Pharmaceutically acceptable salts, derivatives or analogues of any of these compounds may also be used.

Examples of growth inhibitory agents for use in the invention include agents that block cell cycle progression (at a place other than S phase), such as agents that induce G1 arrest and M-phase arrest. Classical M-phase blockers include the vincas (vincristine and vinblastine); taxane family members, including paclitaxel, docetaxel, and analogues thereof; and topoisomerase inhibitors, such as irinotecan, topotecan, camptothecin, lamellarin D, doxorubicin, epirubicin, daunorubicin, etoposide, and bleomycin. Those agents that arrest G1 include, for example, DNA alkylating agents, such as tamoxifen, prednisone, dacarbazine, mechlorethamine, cisplatin, methotrexate, 5-FU, and ara-C.

The choice of chemotherapeutic agent will be dependent on various factors including the nature of the tumor, the patient to be treated, etc., but can readily be selected by those skilled in the art.

In one particular embodiment the chemotherapeutic agent is an anti-metabolite. Anti-metabolites which are particularly suitable for use in the invention include the anti-folates, purine and pyrimidine anti-metabolites and antibiotics. One example of an anti-metabolite which may be used in the treatment of pancreatic cancer is 5-fluorouracil (5-FU).

For use in SDT, the microbubble-chemotherapeutic complex is used in combination with at least one sonosensitiser (e.g. a plurality of sonosensitisers) which is also linked to a microbubble (herein a “microbubble-sonosensitiser complex”). The sonosensitiser may be linked to the same microbubble as the chemotherapeutic agent, or alternatively it may be linked to a separate microbubble. Typically, the two agents will be conjugated to separate microbubbles.

The microbubble-sonosensitiser complex comprises a microbubble attached to or otherwise associated with at least one sonosensitiser, preferably a plurality of sonosensitisers. Where the microbubble is attached to more than one sonosensitiser, these may be the same or different. Generally, however, the sonosensitisers will be identical. To the extent that such a complex is intended for use in methods of SDT, it will be ultrasound-responsive. Specifically, it is intended that the microbubble component of the complex can be ruptured by application of ultrasound, thereby releasing the sonosensitiser at the desired target site. As herein described, activation of the sonosensitiser by acoustic energy also results in the generation of reactive oxygen species, such as singlet oxygen, which are cytotoxic.

The sonosensitiser (or sonosensitisers) may be linked to the microbubble through covalent or non-covalent means, e.g. via electrostatic interaction, van der Waals forces and/or hydrogen bonding. In one embodiment the microbubble is electrostatically bound to the sonosensitiser. In another embodiment it may be covalently bound, i.e. the sonosensitiser will be attached to the microbubble by one or more covalent bonds. Preferably, however, the interaction will involve strong non-covalent bonding such as the biotin-avidin interaction as described above.

In the case where a biotin-avidin interaction is employed to link the sonosensitiser (or sonosensitisers) to the microbubble, one component of the binding pair (e.g. the sonosensitiser) is functionalised with biotin and the other (e.g. the microbubble) with avidin. Typically, the avidin molecule will also be bound to the microbubble via a biotin-avidin interaction. For example, a microbubble may be functionalised with biotin to form a biotinylated microbubble which is then incubated with avidin. Once the avidin is bound to the bubble, this permits binding of any further biotinylated moieties, such as the sonosensitiser. The resulting linkage between the microbubble and the sonosensitiser may thus take the form a “biotin-avidin-biotin” interaction.

As used herein, the term “microbubble” is intended to refer to a microsphere comprising a shell having an approximately spherical shape and which surrounds an internal void which comprises a gas or mixture of gases. The “shell” refers to the membrane which surrounds the internal void of the microbubble.

Microbubbles are well known in the art, for example as ultrasound contrast agents. Their composition and methods for their preparation are thus well known to those skilled in the art. Examples of procedures for the preparation of microbubbles are described in, for example, Christiansen et al., Ultrasound Med. Biol., 29: 1759-1767, 2003; Farook et al., J. R. Soc. Interface, 6:271-277, 2009; and Stride & Edirisinghe, Med. Biol. Eng. Comput., 47:883-892, 2009, the contents of which are hereby incorporated by reference.

Microbubbles comprise a shell which surrounds an internal void comprising a gas. Generally, these are approximately spherical in shape, although the shape of the microbubble is not essential in carrying out the invention and is therefore not to be considered limiting. The size of the microbubble should be such as to permit its passage through the pulmonary system following administration, e.g. by intravenous injection. Microbubbles typically have a diameter of less than about 200 μm, preferably in the range from about 0.5 to about 100 μm. Particularly suitable for use in the invention are microbubbles having a diameter of less than about 10 μm, more preferably 1 to 8 μm, particularly preferably up to 5 μm, e.g. about 2 μm. The shell of the microbubble will vary in thickness and will typically range from about 10 to about 200 nm. The precise thickness is not essential provided that the shell performs the desired function of retaining the gas core.

Materials which may be used to form the microbubbles should be biocompatible and suitable materials are well known in the art. Typically, the shell of the microbubble will comprise a surfactant or a polymer. Surfactants which may be used include any material which is capable of forming and maintaining a microbubble by forming a layer at the interface between the gas within the core and an external medium, e.g. an aqueous solution which contains the microbubble. A surfactant or combination of surfactants may be used. Those which are suitable include lipids, in particular phospholipids. Lipids which may be used include lecithins (i.e. phosphatidylcholines), e.g. natural lecithins such as egg yolk lecithin or soya bean lecithin and synthetic lecithins such as dimyristoylphosphatidylcholine, dipalmitoylphosphatidylcholine or distearoylphosphatidylcholine; phosphatidic acids; phosphatidylethanolamines; phosphatidylserines; phosphatidylglycerols; phosphatidylinositols; and mixtures thereof. The use of phospholipids having a net overall charge (e.g. a negative charge) such as, for example, those derived from soya bean or egg yolk; phosphatidylserines; phosphatidylglycerols; phosphatidylinositols; and phosphatidic acids, is advantageous for ionic linkage of the microbubble to the sonosensitiser. In one embodiment, longer chain lipids such as dibehenoylphosphatidyl choline (DBPC) may be used to form the shell of the microbubbles.

Suitable lipids may be selected based on their ability to enhance the stability of the microbubbles with regard to oxygen retention. Suitable for use in this regard is dibehenoylphosphatidyl choline (DBPC).

Polymer materials which are suitable for use in forming the shell of the microbubble include proteins, in particular albumin, particularly human serum albumin. Other biocompatible polymers which may be used include poly (vinyl alcohol) (PVA), poly(D,L-lactide-co-glycolide) (PLGA), cyanoacrylate, poloxamers (Pluronics) or combinations thereof.

The microbubble shells may comprise single or multiple layers of the same or different materials. Multiple layers may, for example, be formed in cases where the basic shell material (e.g. a lipid) bears one or more polymers or polysaccharides. Examples of such polymers include polyethylene glycol and polyvinylpyrrolidone. The microbubble shell may also be coated with polymers, such as poly-L-lysine and PLGA, and/or polysaccharides, such as alginate, dextran, diethylamino-ethyl-dextran hydrochloride (DEAE) or chitosan. Methods for attaching these coating materials may involve electrostatic or covalent interactions. Different coating materials (polymers, polysaccharides, proteins, etc.) may be used in order to improve the properties of the microbubble, for example by increasing the rigidity, stability in circulation and/or tissue permeation capability of the microbubble-based reagents, by manipulating the net surface charge of the microbubble and, perhaps most importantly, by increasing its payload capacity. One way of achieving an increase in payload capacity is by the application of the layer-by-layer (LBL) assembly technique. This involves the attachment of multiple layers of a sonosensitiser onto preformed microbubbles in order to increase the sonosensitiser loading capacity. The LBL technique is described by Borden et al. in DNA and polylysine adsorption and multilayer construction onto cationic lipid-coated microbubbles, Langmuir 23 (18): 9401-8, 2007.

In addition, coating of the microbubbles can increase stability of the payload, particularly when the coating material serves as an immobilisation matrix for the sonosensitiser or chemotherapeutic agent (e.g. via cross-linking).

Lipids forming either a monolayer, bilayer or multilamellar structure may also be used. Examples of these include unilamellar or multilammellar liposomes and micelles.

Any of the microbubble shells herein described may comprise further components which aid delivery of the bubble to the target site. For example, these may be functionalised such that these incorporate or have bound thereto a ligand or targeting agent which is able to bind to a target cell or tissue. Examples of suitable targeting agents include antibodies and antibody fragments, cell adhesion molecules and their receptors, cytokines, growth factors and receptor ligands. Such agents can be attached to the microbubbles using methods known in the art, e.g. by covalent coupling, the use of molecular spacers (e.g. PEG) and/or the avidin-biotin complex method. For example, the incorporation of a lipid-PEG-biotin conjugate in lipid-based microbubbles followed by the addition of avidin enables functionalisation of the microbubble surface with a biotinylated targeting ligand. Herceptin is an example of an antibody which may be conjugated to the microbubble shell for targeting purposes.

The gas within the core of the microbubble should be biocompatible. The term "gas" encompasses not only substances which are gaseous at ambient temperature and pressure, but also those which are in liquid form under these conditions. Where the "gas" is liquid at ambient temperature this will generally undergo a phase change to a gas at a temperature of 30° C. or above, more preferably 35° C. or above. For any gas which is a liquid at ambient temperature, it is generally preferred that this will undergo a phase change to a gas at a temperature between about 30 and 37° C., preferably at around normal body temperature. Any reference herein to "gas" should thus be considered to encompass not only gases and liquids, but also liquid vapours and any combination thereof, e.g. a mixture of a liquid vapour in a gas.

Gases which are suitable for incorporation within the microbubbles for use according to the invention include air, nitrogen, oxygen, carbon dioxide, hydrogen; inert gases such as helium, argon, xenon or krypton; sulphur fluorides such as sulphur hexafluoride, disulphur decafluoride; low molecular weight hydrocarbons such as alkanes (e.g. methane, ethane, propane, butane), cycloalkanes (e.g. cyclopropane, cyclobutane, cyclopentane), alkenes (e.g. ethylene, propene); and alkynes (e.g. acetylene or propyne); ethers; esters; halogenated low molecular weight hydrocarbons; and mixtures thereof.

Examples of suitable halogenated hydrocarbons are those which contain one or more fluorine atoms and include, for example, bromochlorodifluoromethane, chlorodifluoromethane, dichlorodifluoromethane, bromotrifluoromethane, chlorotrifluoromethane, chloropentafluoroethane, dichlorotetrafluoroethane, chlorotrifluoroethylene, fluoroethylene, ethyl fluoride, 1,1-difluoroethane and perfluorocarbons.

Examples of suitable fluorocarbon compounds include perfluorocarbons. Perfluorocarbons include perfluoroalkanes such as perfluoromethane, perfluoroethane, perfluoropropanes, perfluorobutanes, perfluoropentanes, perfluorohexanes and perfluoroheptanes; perfluoroalkenes such as perfluoropropene, perfluorobutenes; and perfluorocycloalkanes such as perfluorocyclobutane.

Microbubbles containing perfluorinated gases, in particular, perfluorocarbons such as perfluoropropanes, perfluorobutanes, perfluoropentanes and perfluorohexanes are suitable for use in the invention due to their stability in the bloodstream.

Microbubbles containing a perfluorocarbon, particularly a perfluoroalkane, and a shell comprising a phospholipid may be used in the invention and are described in, for example, Nomikou & McHale, Cancer Lett., 296:133-143, 2010. One example of such a microbubble is Sonidel SDM202 (available from Sonidel Ltd.). The perfluorocarbon may either be present as a gas or in liquid form. Those containing a liquid core may be prepared from nanoemulsions which may subsequently be converted to a gas microbubble upon exposure to ultrasound, e.g. as described in Rapoport et al., Bubble Sci. Eng. Technol. 1:31-39, 2009.

Particularly preferred for use in the invention are microbubbles which carry oxygen. As oxygen is a key substrate for SDT and many cancers are hypoxic, filling the core of the bubble with oxygen gas enhances the sonodynamic effect and the amount of singlet oxygen produced.

Where a microbubble is loaded with both the chemotherapeutic agent and the sonosensitiser, the bubble will preferably carry oxygen (e.g. it will contain oxygen gas). In the case where different microbubbles are used in a combination therapy as herein described it is preferred that at least one type of microbubble will incorporate oxygen. For example, the microbubble conjugated to the sonosensitiser may include oxygen and/or the microbubble carrying the chemotherapeutic agent may include oxygen. In a preferred embodiment, all microbubbles used will carry oxygen (e.g. $O_2$ gas), i.e. these will be "$O_2$-loaded".

Sonosensitisers which may be used in the invention include compounds which render target cells or tissues hyper-sensitive to ultrasound. In some cases, a sonosensitiser may be capable of converting acoustic energy (e.g. ultrasound) into ROS that result in cell toxicity. Others may render the target cell or tissues hypersensitive to ultrasound by compromising the integrity of the cell membrane. It is well known that many known sonosensitisers can facilitate photodynamic activation and can also be used to render cells or tissues hypersensitive to light.

In one embodiment of the invention the sonosensitiser may simultaneously function as an imaging agent, for example as a NIR agent. Such sensitisers offer benefit in terms of their imaging potential enabling tracking of the conjugates in vivo.

Examples of compounds suitable for use as sonosensitisers in the invention include phenothiazine dyes (e.g. methylene blue, toluidine blue), Rose Bengal, porphyrins (e.g. Photofrin®), chlorins, benzochlorins, phthalocyanines, napthalocyanines, porphycenes, cyanines (e.g. Merocyanine 540 and indocyanine green), azodipyromethines (e.g. BODIPY and halogenated derivatives thereof), acridine dyes, purpurins, pheophorbides, verdins, psoralens, hematoporphyrins, protoporphyrins and curcumins. Any known analogues or derivatives of these agents may also be used. Suitable derivatives include the pharmaceutically acceptable salts.

Preferred for use as sonosensitisers in the invention are methylene blue, Rose Bengal, indocyanine green (ICG, also known as Cardio Green), and any analogues and derivatives thereof. ICG has the following structure:

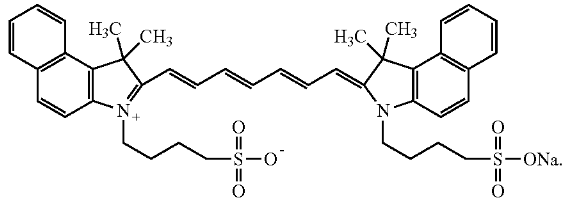

Known analogues of any of the sonosensitisers described herein may also be used in the invention. Particularly suitable are structural analogues of the cyanine-based dyes, e.g. structural analogues of ICG and their pharmaceutically acceptable salts. Examples of these include the cyanine dyes IR820 and IR783, both of which are commercially available:

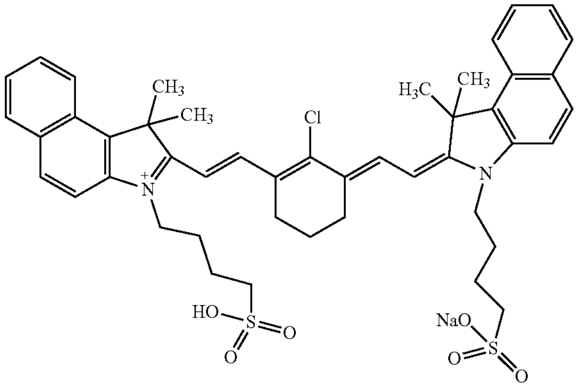

IR820

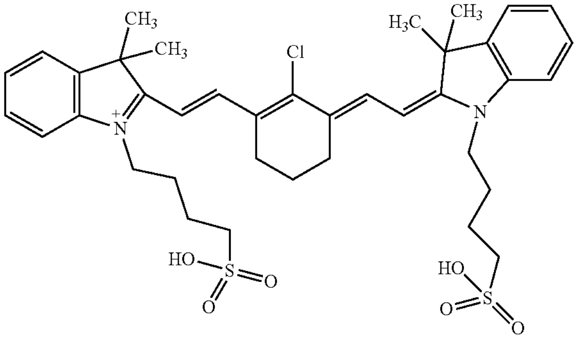

IR783

The near-infrared (NIR) absorbing fluorescent dye ICG is FDA approved for use in medical imaging. It absorbs strongly in the NIR region (750-900 nm) and has the advantage that this can be activated by light at a greater depth in human tissue (the penetration of light at 800 nm is four times greater than at 600 nm). However, the singlet oxygen generation (SOG) effectiveness of cyanine dyes such as ICG, IR820 and IR783 is relatively poor when compared to other known sensitisers such as Rose Bengal. This can be overcome by concentrating more cyanine molecules onto the microbubble.

Other attempts have been made to improve the ROS generating capability of cyanine dyes by incorporation of halogen atoms (e.g. iodine and bromine) into their structure. For example, in US 2013/0231604 (the entire contents of which are incorporated herein by reference) it is proposed that cyanine-based dyes and analogues of such dyes may be modified by incorporation of three iodine atoms on the benzene or napthalene portion of each benzazole or napthazole ring. Any of the polymethine dyes (in particular the cyanines) disclosed in this document may be used as sonosensitisers in the present invention.

In a development of the work documented in US 2013/0231604, the present inventors have prepared structural analogues of certain cyanine dyes (e.g. IR783) carrying either one or two halogen atoms (e.g. iodine or bromine, preferably iodine) on each of the benzazole rings and found these have enhanced ROS generating capability and are thus more cytotoxic to cancer cells (e.g. pancreatic cancer cells) upon ultrasound activation compared to ICG. Although not wishing to be bound by theory, the presence of the halogen atoms is believed to increase intersystem crossing (ISC) from the excited singlet to the excited triplet state due to what is known as the "heavy atom effect". The triplet excited state is then able to engage with molecular oxygen or other substrates to generate ROS. That such a level of enhanced ROS generating capability may be achieved by replacing fewer (i.e. a total of either 2 or 4) hydrogen atoms in IR783 with halogen atoms (e.g. iodine) could not be predicted in light of the teaching of US 2013/0231604.

Furthermore, as will be discussed in more detail below, the inventors have surprisingly found that when IR783 is substituted with a total of two halogen atoms (i.e. just one halogen atom, e.g. iodine, on each of the benzazole rings), the compound remains highly fluorescent and thus can also be used as a NIR imaging agent. Since any increase in ISC typically reduces the ability of a compound to emit fluorescence, this finding is unexpected. Combined, the NIR imaging potential and sensitiser potential of these particular analogues of IR783 means these compounds have "theranostic" potential, i.e. the ability to function both as a therapeutic and diagnostic agent.

The halogenated (e.g. iodinated) analogues of IR783 which are disclosed herein are new chemical entities and represent a further aspect of the invention. Viewed from a further aspect the invention thus provides a compound of formula I or formula II, or a pharmaceutically acceptable salt thereof:

(I)

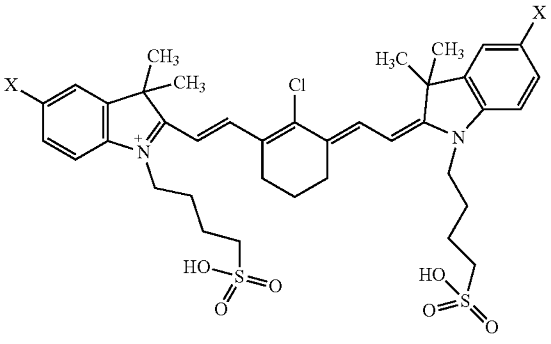

-continued (II)

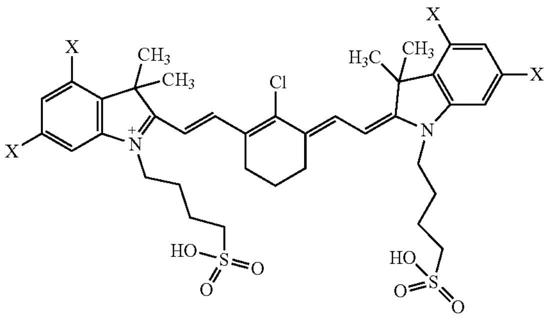

(wherein in formula I and formula II each X is independently selected from a bromine and iodine atom, preferably wherein each X is iodine).

Suitable salts of such compounds and methods for their preparation may readily be selected by those skilled in the art. The compounds may, for example, be converted into a suitable pharmaceutically acceptable salt thereof with an inorganic or organic base. Bases which may be suitable for this purpose include alkali and alkaline earth metal hydroxides, e.g. sodium hydroxide, potassium hydroxide or cesium hydroxide, ammonia and organic amines such as diethylamine, triethylamine, ethanolamine, diethanolamine, cyclohexylamine and dicyclohexylamine. Procedures for salt formation are conventional in the art.

Preferred compounds of formula I and II include the following and their pharmaceutically acceptable salts:

(Ia)

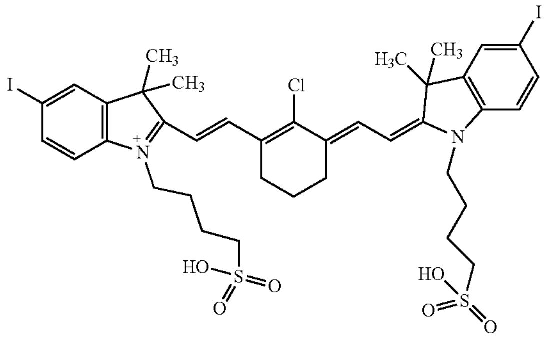

(IIa)

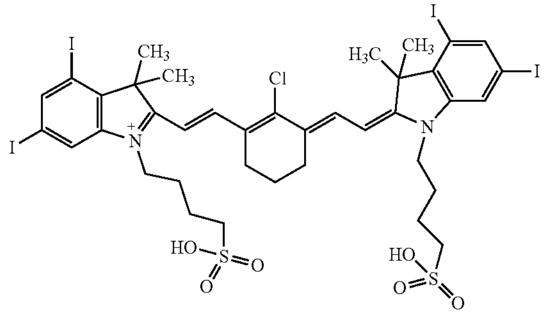

Pharmaceutical compositions containing any of the compounds of formula I, II, Ia or IIa, or a pharmaceutically acceptable salt thereof, together with at least one pharmaceutically acceptable carrier or excipient represent a further aspect of the invention.

These novel compounds may be prepared by methods known to those skilled in the art and are illustrated by way of the examples provided herein. Methods for the preparation of such compounds also form part of the invention.

Viewed from a further aspect the invention thus provides a method for the preparation of a compound of formula I or II, said method comprising the following steps:

(a) reacting a compound of formula III:

(III)

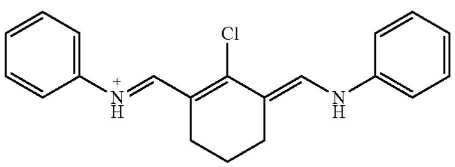

with a compound of formula IV or V:

(IV)

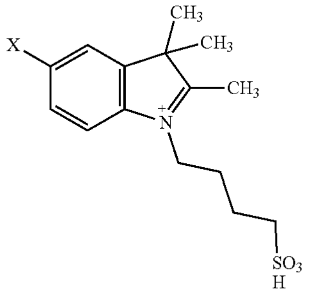

(V)

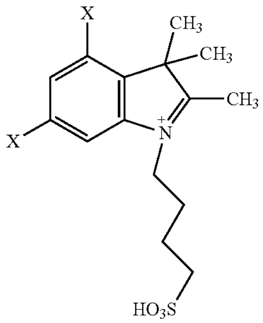

(wherein, in formula IV, X is a bromine or iodine atom, and in formula V each X is independently selected from a bromine and iodine atom); and (b) optionally converting the resulting compound into a pharmaceutically acceptable salt thereof.

The invention further provides for the use of any of the compounds of formula I, II, Ia and IIa, and their pharmaceutically acceptable salts, as a medicament, for example as a therapeutic, diagnostic or theranostic agent (i.e. one having both therapeutic and diagnostic functionality). In particular, these may be used in a method of PDT and/or SDT, or in a method of in vivo imaging (e.g. NIR imaging), particularly in such methods for the treatment and/or diagnostic imaging of deeply seated cells, such as tumor masses. When used in methods of PDT, activating light having a wavelength in the near-IR region, for example from 700 to 900 nm, more particularly from 750 to 850 nm, may be employed. Upon NIR light activation or ultrasound activation, these compounds have enhanced ROS generating capability and are more toxic to cancer cells (e.g. pancreatic and cervical cancer cells) than ICG.

Use of the compounds of formula I or Ia, or their pharmaceutically acceptable salts, as NIR imaging agents, preferably as combined sensitiser and NIR imaging agents in PDT and/or SDT, represents a preferred embodiment of the invention.

Microbubbles carrying any of the halogenated sensitisers described herein, particularly the compounds of formula I, II, Ia, IIa, and their pharmaceutically acceptable salts, and methods for the preparation of such microbubbles also form part of the invention. Such microbubble-sensitiser complexes may be produced using any of the methods herein described in respect of the attachment of a sonosensitiser to a microbubble. Preferably such methods will comprise the step of biotinylation of the halogenated sensitiser and linkage of this to a biotin-avidin-functionalised microbubble.

Methods for the formation of microbubbles are known in the art. Such methods include the formation of a suspension of the gas in an aqueous medium in the presence of the selected shell material. Techniques used to form the microbubble include sonication, high speed mixing (mechanical agitation), coaxial electrohydrodynamic atomisation and microfluidic processing using a T-junction (see e.g. Stride & Edirisinghe, Med. Biol. Eng. Comput., 47:883-892, 2009). Sonication is widely used and generally preferred. This technique may be carried out using an ultrasound transmitting probe. More particularly, an aqueous suspension of the microbubble shell components is sonicated in the presence of the relevant microbubble component gas, e.g. oxygen.

Other methods which may be used to form the microbubbles include vaporisation of a nanodroplet core in a nanoemulsion (see e.g. Rapoport et al., supra). The core of such nanodroplets will typically be formed by an organic perfluorocompound which is encased by walls of a biodegradable amphiphilic block copolymer such as poly(ethylene oxide)-co-poly(L-lactide) or poly(ethylene oxide)-co-caprolactone. Alternatively, nanoemulsions may be prepared by extrusion through sizing membranes, for example using albumin as the shell material. The droplet-to-bubble transition may be induced by physical and/or mechanical means which include heat, ultrasound and injection through a fine-gauge needle. Such microbubbles may be formed at the point of administration to the patient (e.g. during the step of administration using a fine-gauge needle) or in vivo at the desired target cells or tissues (e.g. by subjecting the nanoemulsion to ultrasound).

Administration of a nanoemulsion which is capable of forming the desired microbubble complex (or complexes) as herein defined, either during the step of administration to the patient or post-administration (i.e. in vivo), is within the scope of the present invention. Where it is desired that the resulting microbubble contains oxygen gas, this may be provided in dissolved form in a liquid perfluorocarbon core of a phase-shift nanoemulsion.

The microbubble complexes herein described may be prepared using methods and procedures known in the art. Methods which may be used for covalently attaching the chemotherapeutic agent and/or the sonosensitiser to a microbubble include known chemical coupling techniques. The exact method used will be dependent on the exact nature of the microbubble, the chemotherapeutic agent and the sonosensitiser, specifically the nature of any pendant functional groups. If necessary, one or both components of the complex (i.e. the microbubble and/or sonosensitiser, or the microbubble and/or chemotherapeutic agent) may be functionalised, e.g. to include reactive functional groups which may be used to couple the molecules. Suitable reactive groups include acid, hydroxy, carbonyl, acid halide, thiol and/or primary amine. Methods for the introduction of such functional groups are well known in the art.

Examples of methods which may be used to covalently link a microbubble to one or more chemotherapeutic agents and/or sonosensitisers include, but are not limited to, the following: a) Carbodiimide based coupling methods. These may be used to couple microbubbles containing either an amine or carboxylic acid functionality to a moiety having either a carboxylic acid or amine functionality. Such methods result in the formation of ester or amide bonds; b) "CLICK" reaction (i.e. 1,3-dipolar cycloaddition reaction). This may be used to react azide or acetylene functionalised microbubbles with a moiety having either acetylene or azide functionality; c) Schiff base formation (i.e. imine bond formation). This reaction may be used to bond aldehyde or amine functionalised microbubbles to a moiety containing amine or aldehyde functionality; and d) Michael addition reaction.

Linkage of the microbubble to one or more chemotherapeutic agents and/or sonosensitisers via the biotin-avidin linkage may be carried out by methods known to those skilled in the art. In such methods, both moieties will typically be biotinylated and avidin then used to form the linkage between the two. An example of a method to produce a microbubble-chemotherapeutic agent conjugate bound via a biotin-avidin interaction is provided in scheme 1 in Example 2.

As an alternative to coupling of the chemotherapeutic agent and/or sonosensitiser to a pre-formed microbubble, these moieties may alternatively be linked to a lipid (e.g. using any of the methods described above) and that lipid may subsequently be incorporated into the lipid shell of the microbubble during its preparation.

Charged sonosensitisers and/or chemotherapeutic agents may be electrostatically linked to a charged microbubble. For example, an anionic bubble may be linked to a cationic sonosensitiser or cationic chemotherapeutic agent and vice versa. One example of a charged sonosensitiser is methylene blue which may be electrostatically attached to an anionic microbubble.

Examples of methods for the preparation of a microbubble-sonosensitiser complex are disclosed in WO 2012/143739, the entire contents of which are incorporated herein by reference. By way of example, attached FIG. 2 shows (a) a schematic illustration of the preparation of a Rose Bengal derivative (denoted "RB1") and (b) a schematic representation of covalent coupling of RB1 to a microbubble. Any of the methods disclosed in WO 2012/143739 may be applied analogously to the preparation of a microbubble-chemotherapeutic agent complex as herein described.

The microbubble-chemotherapeutic agent complexes as herein described are in themselves novel and form a further aspect of the invention. In one embodiment these complexes may also be linked to one or more sonosensitisers as herein described. Methods for the preparation of the microbubble-chemotherapeutic agent complexes comprising the step of linking at least one chemotherapeutic agent to a microbubble, for example using any of the techniques herein described, form a further aspect of the invention.

The microbubble complexes herein described have properties which render these useful in methods of sonodynamic therapy.

The complexes are suitable for the treatment of disorders or abnormalities of cells or tissues within the body which are responsive to sonodynamic therapy. These include malignant and pre-malignant cancer conditions, such as cancerous growths or tumours, and their metastases; tumours such as sarcomas and carcinomas, in particular solid tumours. The invention is particularly suitable for the treatment of tumours, especially those which are located below the surface of the skin.

Examples of tumours that may be treated using the invention are sarcomas, including osteogenic and soft tissue sarcomas; carcinomas, e.g. breast, lung, cerebral, bladder, thyroid, prostate, colon, rectum, pancreas, stomach, liver, uterine, hepatic, renal, prostate, cervical and ovarian carcinomas; lymphomas, including Hodgkin and non-Hodgkin lymphomas; neuroblastoma, melanoma, myeloma, Wilm's tumour; leukemias, including acute lymphoblastic leukaemia and acute myeloblastic leukaemia; astrocytomas, gliomas and retinoblastomas. Treatment of pancreatic cancer forms a preferred aspect of the invention.

In one aspect, the complexes herein described may be used in a method of sonodynamic therapy and, simultaneously, a method of in vivo imaging (e.g. a method of diagnostic imaging). In such methods, imaging may be used to monitor payload deposition and/or accumulation of the complex (or complexes) at the target site of interest. As described above, this aspect of the invention may be realised by selection of a sensitiser which has imaging potential, e.g. a sensitiser which simultaneously functions as a NIR imaging agent. Alternatively a known imaging agent, such as a NIR imaging agent, may also be conjugated to at least one of the microbubbles proposed for use in the invention. Where a single microbubble is employed this may thus carry the chemotherapeutic agent, the sonosensitiser and the NIR imaging agent. Where different microbubbles are used to carrying the chemotherapeutic agent and the sonosensitiser, the NIR imaging agent may be conjugated (e.g. via a non-covalent linkage such as a biotin-avidin interaction) to one or both types of microbubble. Each of these types of microbubble is new and these form further aspects of the invention.

In addition to providing a means of targeting a chemotherapeutic agent and a sonosensitiser to a particular site in vivo, the methods herein described may further be exploited ex vivo. For example, in autologous bone marrow transplantation in the treatment of leukaemia, bone marrow from the patient may be treated ex vivo by molecular targeting of the microbubble complex (or complexes) to cancerous cells. These mixtures may then be treated with ultrasound to destroy the cancerous cells and the treated marrow may then be used to re-establish haematopoiesis in the patient following radiation treatment. Alternatively, the methods of the invention may be carried out ex vivo to remove unwanted tissues from organs harvested for conventional transplant. Surgically removed tissues may be targeted and lesions destroyed prior to re-transplantation of the treated tissue.

For use in any of the methods herein described, the microbubble complexes will generally be provided in a pharmaceutical composition together with at least one pharmaceutically acceptable carrier or excipient. Such compositions form a further aspect of the invention.

The pharmaceutical compositions for use according to the invention may be formulated using techniques well known in the art. The route of administration will depend on the intended use. Typically, these will be administered systemically and may thus be provided in a form adapted for parenteral administration, e.g. by intradermal, subcutaneous, intraperitoneal or intravenous injection. Suitable pharmaceutical forms include suspensions and solutions which contain the active microbubble complexes together with one or more inert carriers or excipients. Suitable carriers include saline, sterile water, phosphate buffered saline and mixtures thereof.

The compositions may additionally include other agents such as emulsifiers, suspending agents, dispersing agents, solubilisers, stabilisers, buffering agents, preserving agents, etc. The compositions may be sterilised by conventional sterilisation techniques.

Solutions containing the complexes may be stabilised, for example by the addition of agents such as viscosity modifiers, emulsifiers, solubilising agents, etc.

Preferably, the compositions for use in the invention will be used in the form of an aqueous suspension of the complex (or complexes) in water or a saline solution, e.g. phosphate-buffered saline. The complexes may be supplied in the form of a lyophilised powder for reconstitution at the point of use, e.g. for reconstitution in water, saline or PBS.

The methods herein described involve administration of a therapeutically effective amount of the composition which contains the loaded microbubbles. The microbubble complexes are then allowed to distribute to the desired portion or target area of the body prior to activation. Once administered to the body, the target area is exposed to ultrasound at a frequency and intensity to achieve the desired therapeutic effect. In respect of a sensitiser-loaded microbubble, a typical activation procedure is shown schematically in attached FIG. 1. This shows a two-step process in which the microbubbles (MB) are first ruptured by focused ultrasound thereby releasing the sonosensitiser (SS) which is then able to penetrate the desired target tissue (e.g. tumour). Subsequent sono-activation of the sonosensitiser within the target cells results in production of singlet oxygen which can oxidise various cell components such as proteins, lipids, amino acids and nucleotides thereby destroying the target cells. Whilst it is envisaged that activation of the sonosensitiser will typically take place subsequent to its delivery (i.e. following burst of the microbubbles to release the sonosensitiser), delivery of the complex and activation of the sonosensitiser may nevertheless be simultaneous.

The effective dose of the compositions herein described will depend on the nature of the complex, the mode of administration, the condition to be treated, the patient, etc. and may be adjusted accordingly.

The frequency and intensity of the ultrasound which may be used can be selected based on the need to achieve selective destruction of the microbubble at the target site and may, for example, be matched to the resonant frequency of the microbubble. Ultrasound frequencies will typically be in the range 20 kHz to 10 MHz, preferably 0.1 to 2 MHz. Ultrasound may be delivered as either a single frequency of a combination of different frequencies. Intensity (i.e. power density) of the ultrasound may range from about 0.1 $W/cm^2$ to about 1 $kW/cm^2$, preferably from about 1 to about 50 $W/cm^2$. Treatment times will typically be in the range of 1 ms to 20 minutes and this will be dependent on the intensity chosen, i.e. for a low ultrasound intensity the treatment time will be prolonged and for a higher ultrasound intensity the treatment time will be lower. Ultrasound may be applied in continuous or pulsed mode and may be either focused or delivered as a columnar beam.

Any radiation source capable of producing acoustic energy (e.g. ultrasound) may be used in the methods herein described. The source should be capable of directing the energy to the target site and may include, for example, a probe or device capable of directing energy to the target tissue from the surface of the body.

In cases where the ultrasound frequencies and/or intensities that are needed to achieve cavitation (or microbubble destruction) and those required to cause sonosensitiser activation are different, these different sets of ultrasound parameters (frequency/intensity) may be applied simultaneously or in a two (or multiple)-step procedure.

A further aspect of the invention relates to a method of sonodynamic treatment of cells or tissues of a patient, which method comprises:

(a) administering to the affected cells or tissues an effective amount of a composition as herein described; and
(b) subjecting said cells or tissues to ultrasound.

In the case where the sonosensitiser used is one which also responds to light, ultrasound activation may be accompanied by light activation. Photothermal activation may also additionally be employed, for example when using a NIR dye as the sonosensitiser.

Where different microbubbles are used to carry the chemotherapeutic agent and the sonosensitiser it is envisaged these will generally be co-administered in a single pharmaceutical preparation, e.g. an aqueous solution. However, in another embodiment these may be administered separately (e.g. either simultaneously or sequentially) in separate formulations.

In a further aspect the invention thus provides a product comprising a microbubble-chemotherapeutic agent complex as described herein, and a microbubble-sonosensitiser complex as described herein for simultaneous or sequential use in a method of sonodynamic therapy and/or diagnostic imaging.

In a still further aspect the invention provides a kit comprising: (i) a microbubble-chemotherapeutic agent complex as described herein; and separately (ii) a microbubble-sonosensitiser complex as described herein; optionally together with instructions for the use of (i) and (ii) in a method of sonodynamic therapy and/or diagnostic imaging. When used, the active components of the kit (i.e. (i) and (ii)) may be administered simultaneously, separately or sequentially. In one embodiment of the kit, component (i) and/or (ii) may be provided in dry form, e.g. as lyophilised powders. In this case, the kit may also comprise a container containing a sterile, physiologically acceptable liquid for reconstitution of the powdered forms of the actives, e.g. saline or PBS.

Whilst the various methods and uses according to the invention are primarily described herein in the context of administration of a "ready-to-use" microbubble-sonosensitiser complex, in an alternative embodiment a precursor of the complex may be administered. The term "precursor" as used herein is intended to refer to a precursor for the microbubble-sonosensitiser complex which is converted in vivo to it and is thus essentially equivalent thereto. Thus, for example, the term "precursor" encompasses nanoemulsions or nanodroplet formulations which are capable of conversion to the desired microbubble-sonosensitiser complex either in vivo or during administration. In one embodiment, such precursors are capable of conversion to the desired complex upon accumulation in the target tissue (e.g. tumour tissue). Following distribution to the target tissue or cells, the droplet-to-bubble transition may be triggered by methods which include ultrasound. Alternatively, the step of administration of a precursor of the complex may itself induce formation of a microbubble-sonosensitiser complex according to the invention. For example, where the precursor takes the form of a nanoemulsion, droplet-to-bubble transition may be induced by injection through a fine gauge needle. Direct injection of suitable nanoemulsions into target cells or tissues, for example into tumours, forms a preferred aspect of the invention.

As will be appreciated, in any of the compositions, methods or uses herein described, any reference to a microbubble-sonosensitiser complex according to the invention may be replaced by a suitable "precursor" as defined herein.

Nanoemulsions or nanodroplet formulations for use as microbubble-sonosensitiser precursors according to the invention may be produced by appropriate modification of methods and procedures known in the art, for example those disclosed by Rapoport et al. (supra). In such formulations, the cores of nanoemulsion droplets, which may be formed by a liquid perfluorocarbon (e.g. a perfluoroalkane), are encased by walls of suitable polymeric, protein or lipid shell materials (e.g. any of the polymers described herein in relation to the microbubble-sonosensitiser complexes). Linkage of the shells of the nanodroplets to a sonosensitiser may be achieved using conventional methods and include any of those described above for attaching the sonosensitiser to a pre-formed microbubble. The exact method used will be dependent on the exact nature of the shell material and sonosensitiser, specifically the nature of any pendant functional groups. If necessary, either the shell and/or the sonosensitiser may be functionalised, e.g. to include reactive functional groups which may be used to couple the moieties. Suitable reactive groups include acid, hydroxy, carbonyl, acid halide, thiol and/or primary amine. In one embodiment the shell may be functionalised with biotin and then bound to avidin to subsequently facilitate binding of a biotinylated sonosensitiser. Where it is desired that the formed microbubble will contain oxygen gas, the perfluorocarbon may act as a carrier for the oxygen in liquid form. Following formation of the complex, the perfluorocarbon liquid is saturated with oxygen which subsequently vaporises to form oxygen gas.

In a similar manner to that described above in respect of the microbubble-sonosensitiser complexes, precursors of the microbubble-chemotherapeutic agent complex may also be employed in the invention. Similarly, these may take the form of a nanoemulsion which is capable of forming the desired complex either during administration or at the intended target site.

The invention will now be described further with reference to the following non-limiting Examples and the accompanying drawings in which.

Figure 1:
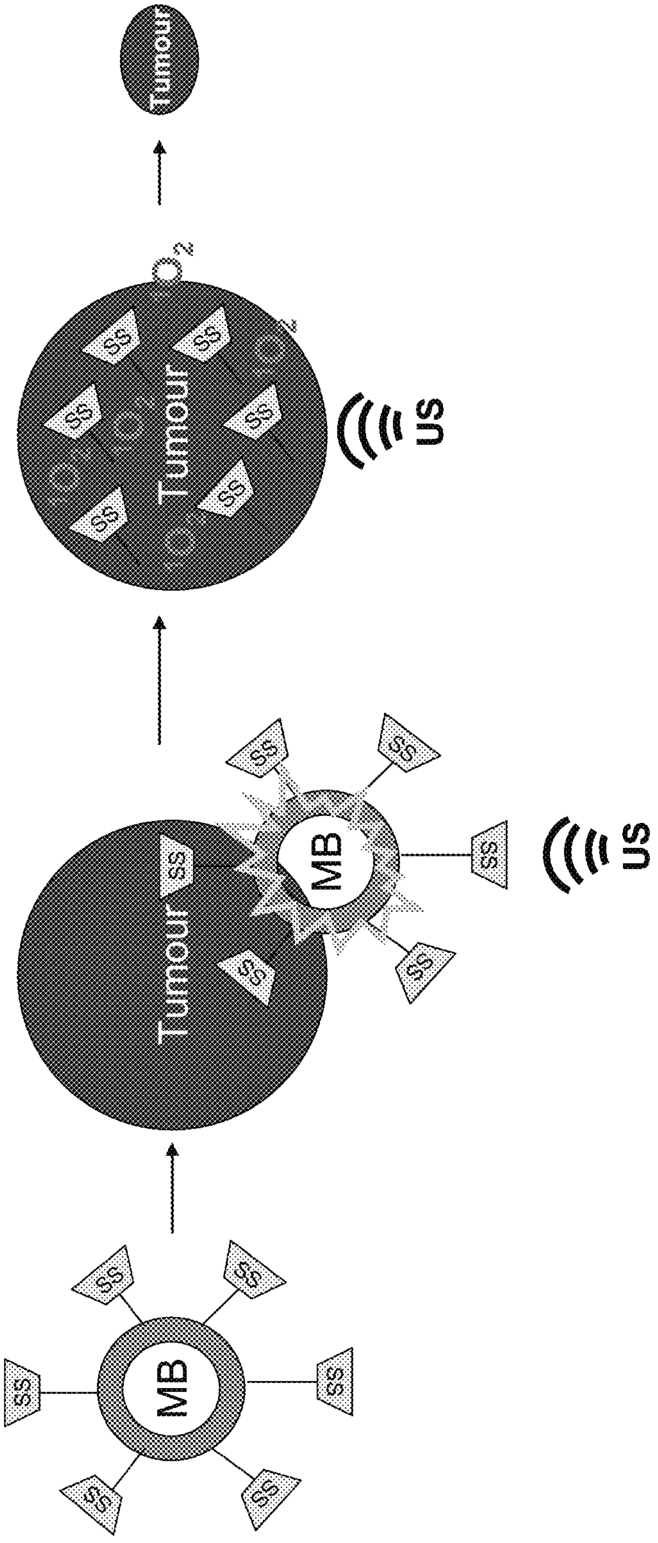
FIG. 1 is a schematic representation of ultrasound-activated sonosensitisation of a microbubble-sonosensitiser complex.
Figure 2:
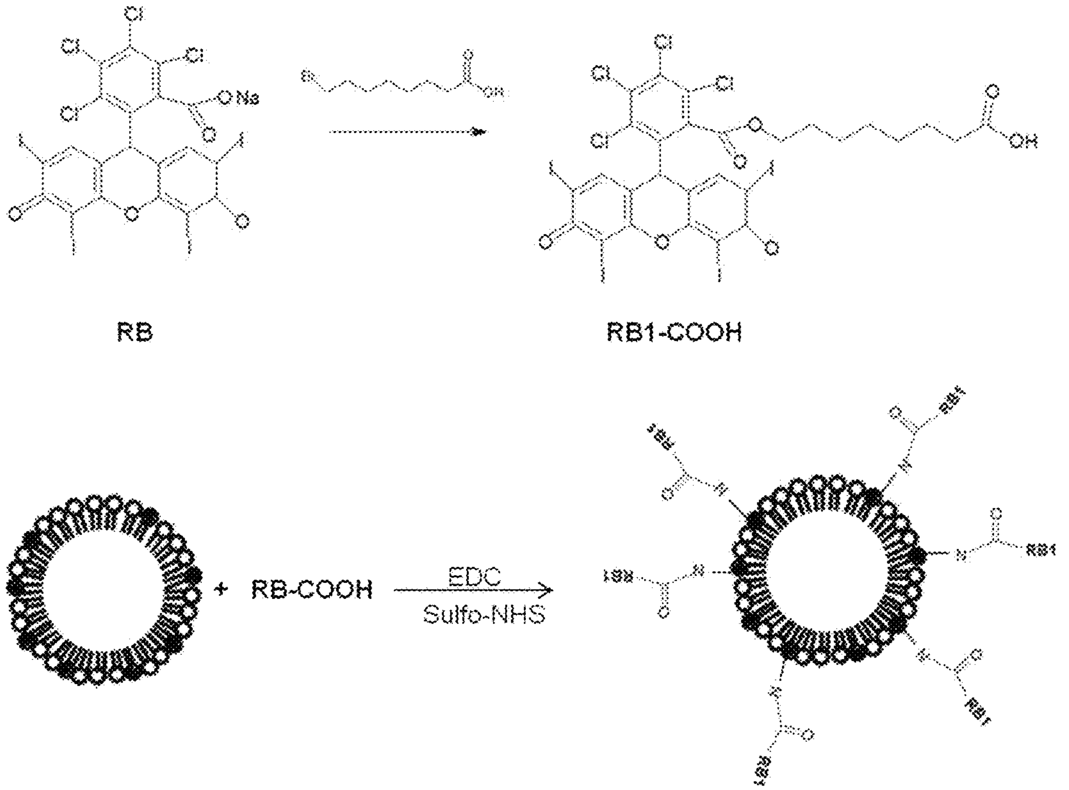
FIG. 2 shows (a) a schematic illustration of the preparation of a Rose Bengal derivative (denoted "RB1") and (b) a schematic representation of covalent coupling of RB1 to a microbubble.
Figure 3:
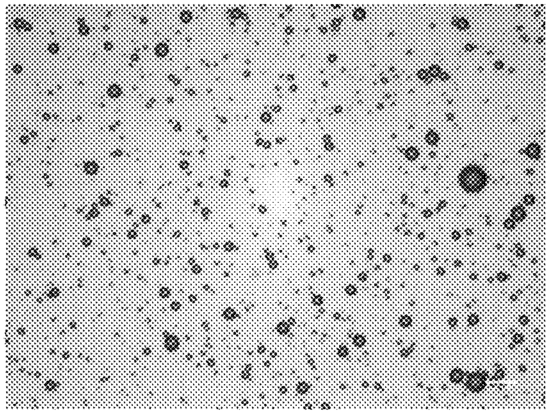
Figure 3:
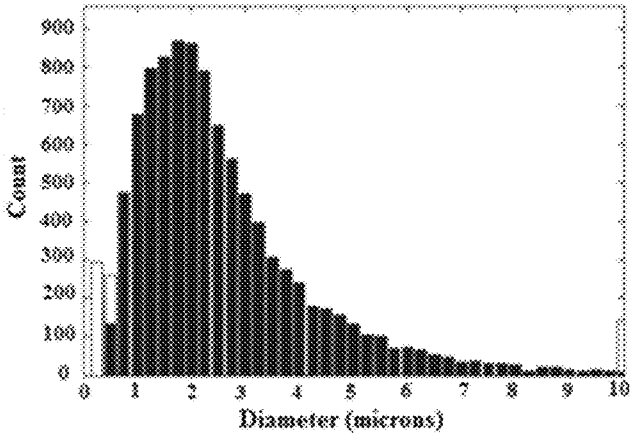

FIG. 3 shows (a) photomicrographs taken with a 40× objective lens of the $O_2$MB after dilution (1:10) in PBS. Scale bar is 20 μm; (b) size distribution of $O_2$MB after centrifugation obtained from analysis of 30 optical microscope images (the unfilled boxes at the left hand side of the graph represent MB that were detected by the image analysis software but smaller than 450 nm, the optical resolution of the system).

Figure 4:
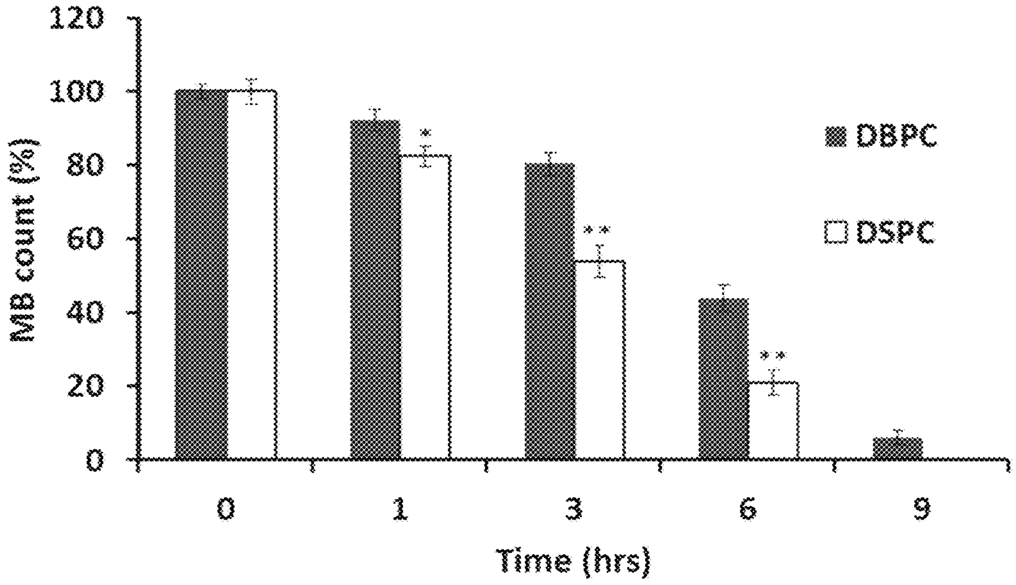

FIG. 4 is a plot of % MB remaining after incubation of PBS dispersions of MBs prepared from either DBPC or DSPC at 37° C. Error bars represent±the standard error where n=4. * $p<0.05$ and  $p<0.01$ FIG. 5** is a plot of % increase in dissolved oxygen for degassed PBS solutions containing either $O_2$MB or PFBMB. Arrow indicates time of ultrasound application.

Figure 6:
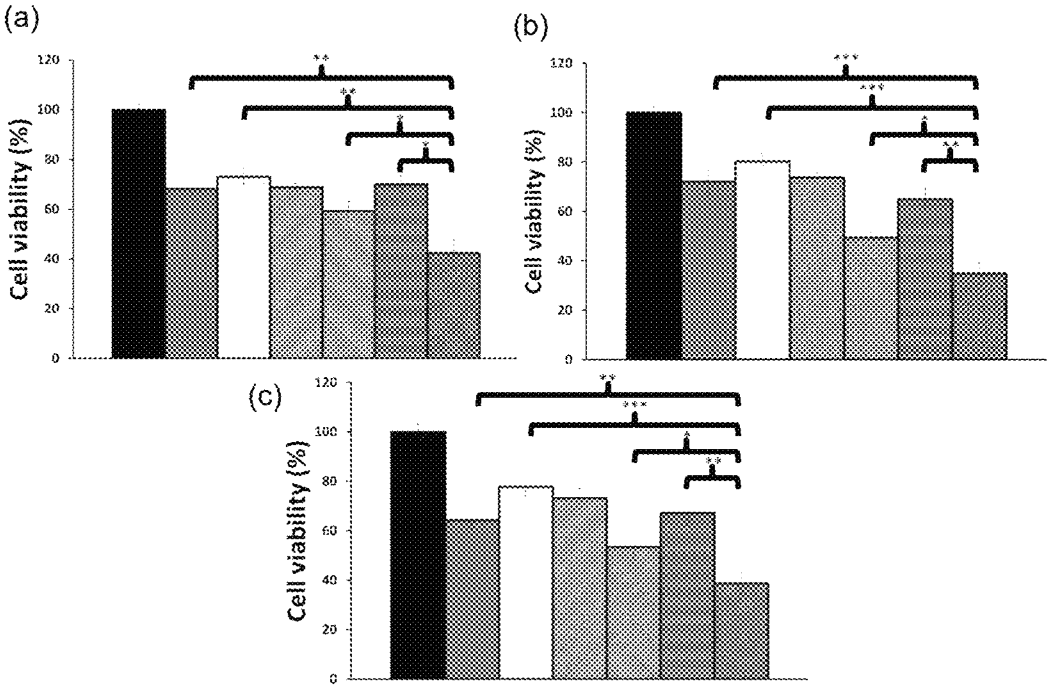

FIG. 6 is a plot of cell viability for (a) BxPc-3, (b) MIA PaCa-2 and (c) PANC-1 cells treated with (from left to right) (i) no treatment (ii) gemcitabine (iii) 5-FU (iv) $O_2$MB-5FU+US (v) $O_2$MB-RB+US (vi) $O_2$MB-RB/$O_2$MB-5FU mix-US and (vii) $O_2$MB-RB/$O_2$MB-5FU mix+US. [RB], [5-FU] and [gemcitabine] were kept constant at 5 μM, 100 μM and 100 μM respectively. Ultrasound treatment was delivered for 30 sec at frequency of 1 MHz, an ultrasound power density of 3.0 $Wcm^{-2}$ and a duty cycle of 50%, pulse frequency=100 Hz. Error bars represent+the standard error where n=4. * $p<0.05$,  $p<0.01$ and * $p<0.001$.

Figure 7:
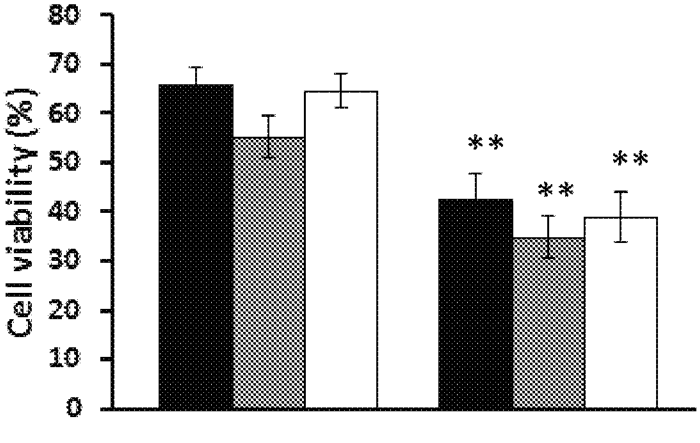
Figure 8:
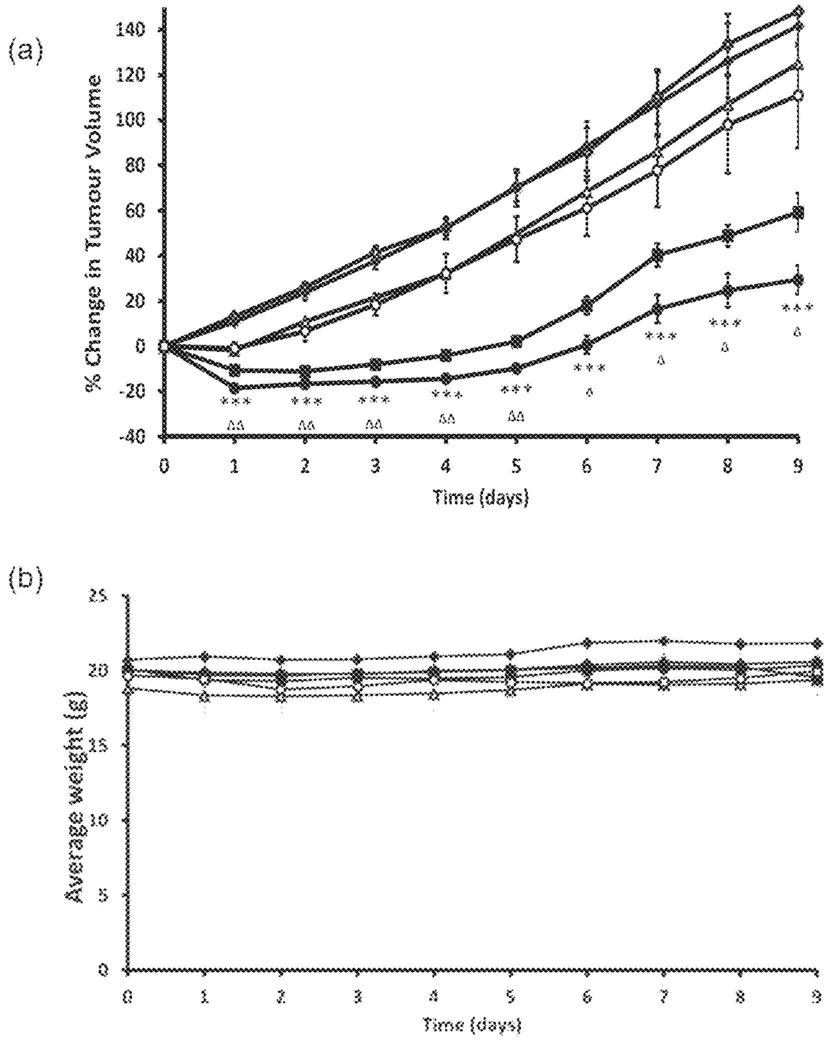

FIG. 7 is a plot of cell viability for BxPc-3 (black), MIA PaCa-2 (grey) and PANC-1 (white) cells treated with PFBMB-RB/PFBMB-5FU mix+US (left) or (ii) $O_2$MB-RB/$O_2$MB-5FU mix+US (right). Concentrations and US parameters as in FIG. 6. Error bars represent±the standard error where n=4  $p<0.01$ FIG. 8** is a plot of (a) % change in tumour volume and (b) average body weight for mice treated with (i) no treatment (open diamonds) (ii) ultrasound only (filled diamonds) (iii) gemcitabine (open triangles) (iv) $O_2$MB-RB/$O_2$MB-5FU mix-US (open circles) (v) $O_2$MB-RB+US (filled squares) (vi) $O_2$MB-RB/$O_2$MB-5FU mix+US (filled circles). Not shown for ease of illustration are treatments with 5-FU alone, $O_2$MB-RB-US, $O_2$MB-5FU+US, $O_2$MB-5FU-US. The RB, 5-FU and gemcitabine concentrations were kept constant in each case at 0.184 mg/kg (90.8 μM), 0.115 mg/kg (440 μM) and 0.264 mg/kg (440 μM) respectively. Ultrasound treatment was delivered for 30 sec at frequency of 1 MHz, an ultrasound power density of 3.0 $Wcm^{-2}$ and a duty cycle of 50%, pulse frequency=100 Hz. Error bars represent+the standard error where n=4. * $p<0.05$,  $p<0.01$ and * $p<0.001$ for (vi) compared to (i) and $^{\Delta}p<0.05$, $^{\Delta\Delta}p<0.01$ and $^{\Delta\Delta\Delta}p<0.001$ for (vi) compared to (v).

Figure 9:
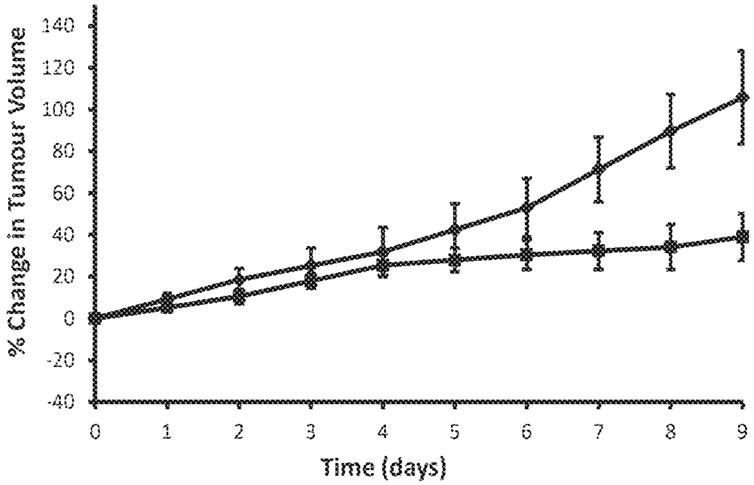

FIG. 9 is a plot of % change in tumour volume for mice treated with IP gemcitabine (120 mg/kg on days 0, 3 and 8) (filled squares) or vehicle only (filled diamonds). Error bars represent+the standard error where n=4.

Figure 10:
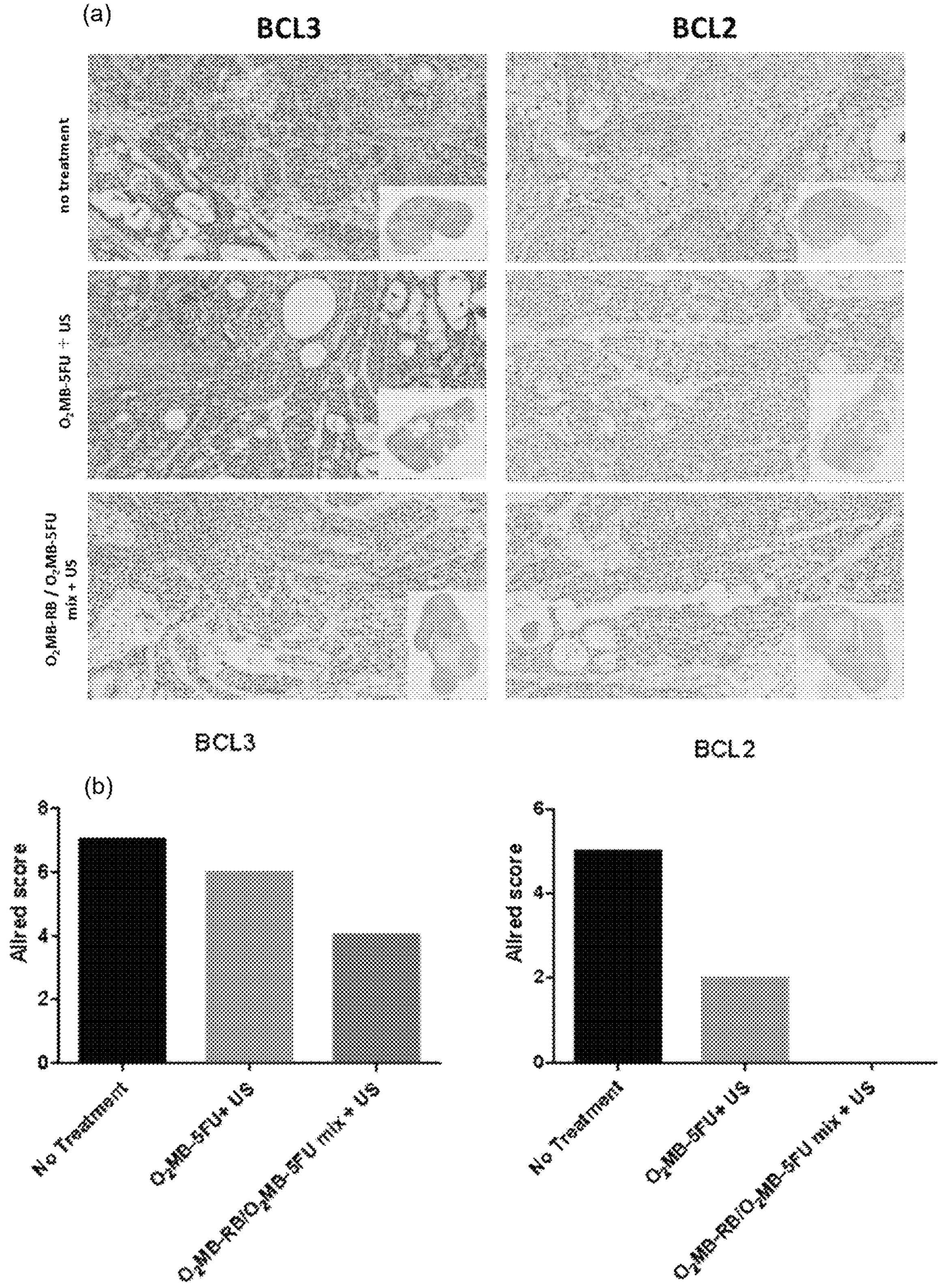

FIG. 10 shows (a) Bcl3 and Bcl2 protein expression using immunohistochemistry. The inner image is the whole section and the main image is a selected area with ×20 magnification. (b) Histology scoring for Bcl3 and Bcl2 expression.

Figure 11:
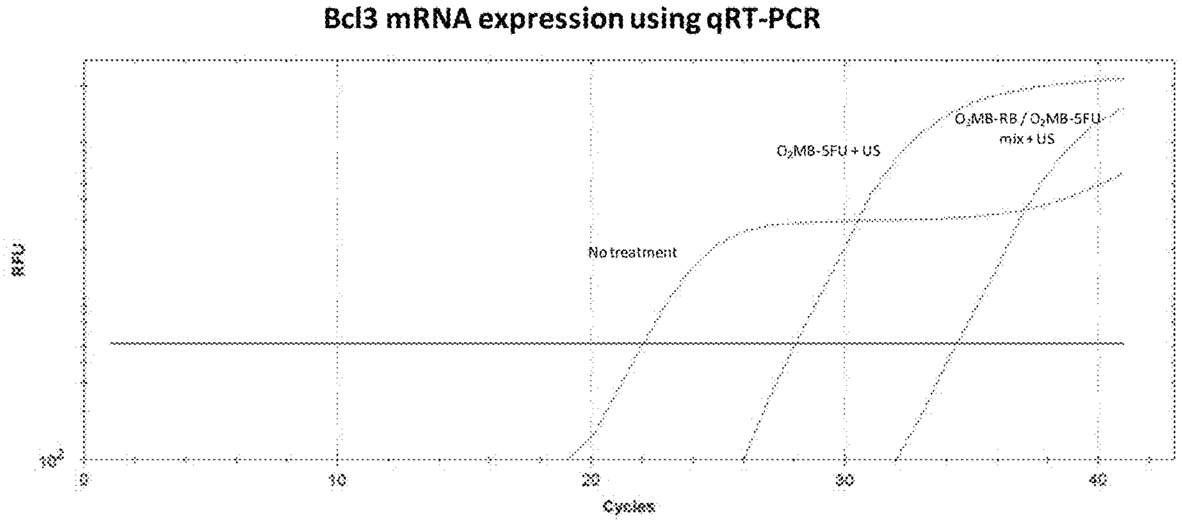
Figure 11:
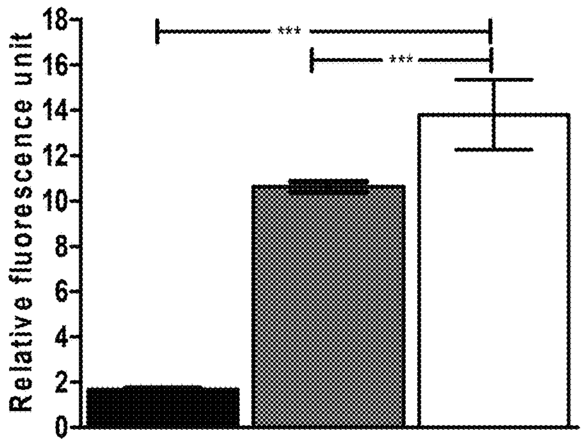

FIG. 11 shows (a) Quantitative RT-PCR mRNA expression of Bcl3. (b) Plot of Bcl3 gene expression profiles for (i) no treatment (black), (ii) $O_2$MB-5FU+US (grey) and (iii) $O_2$MB-RB/$O_2$MB-5FU mix+US (white). Error bars represent+the standard deviation where n=3. *** $p<0.001$.

Figure 12:
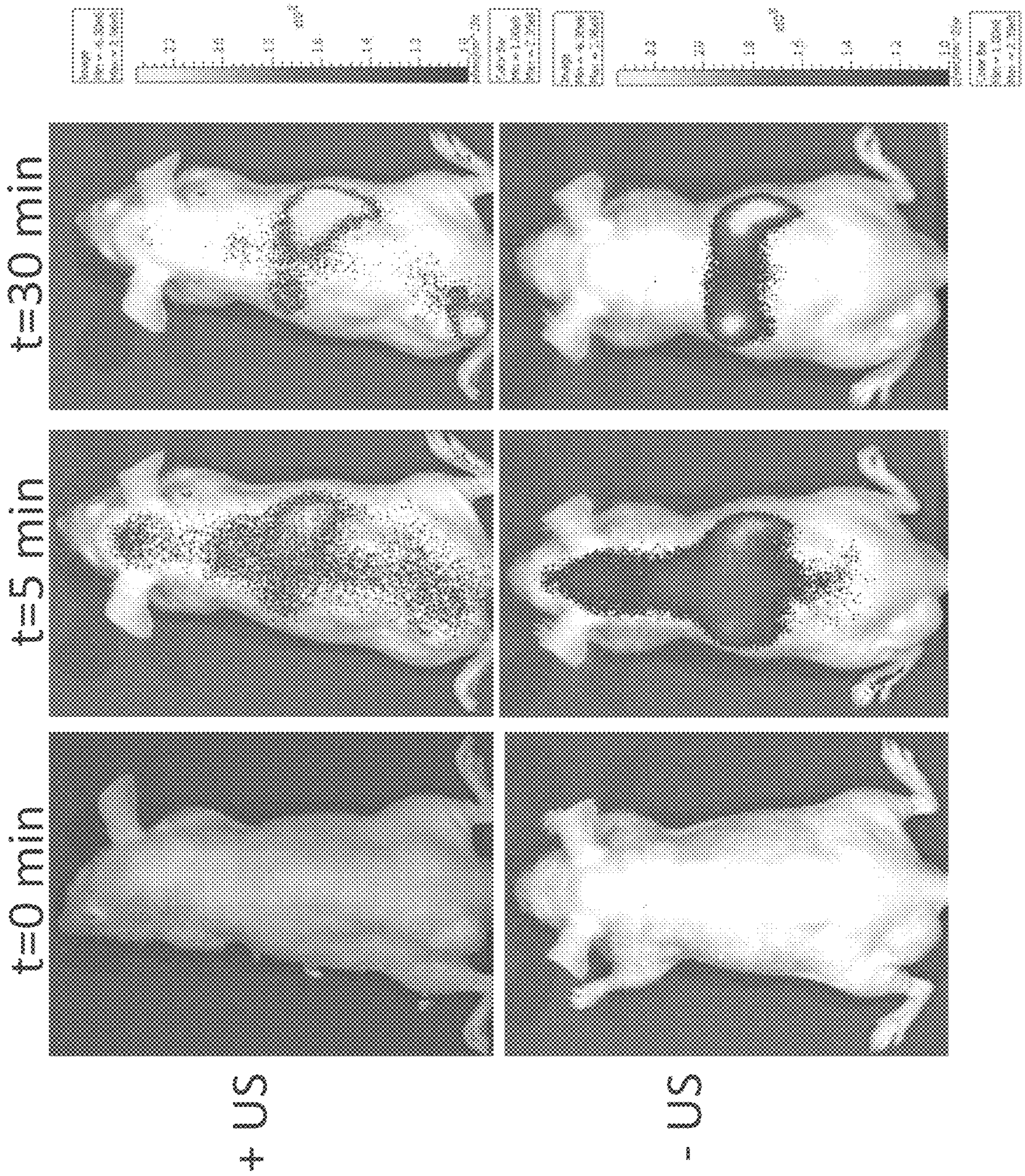
Figure 12:
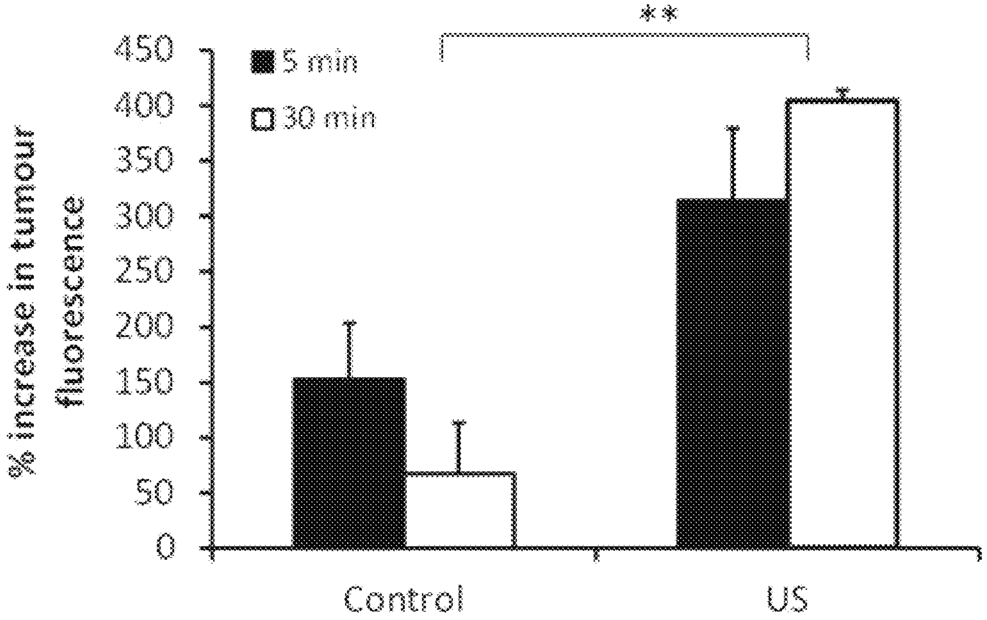
Figure 12:
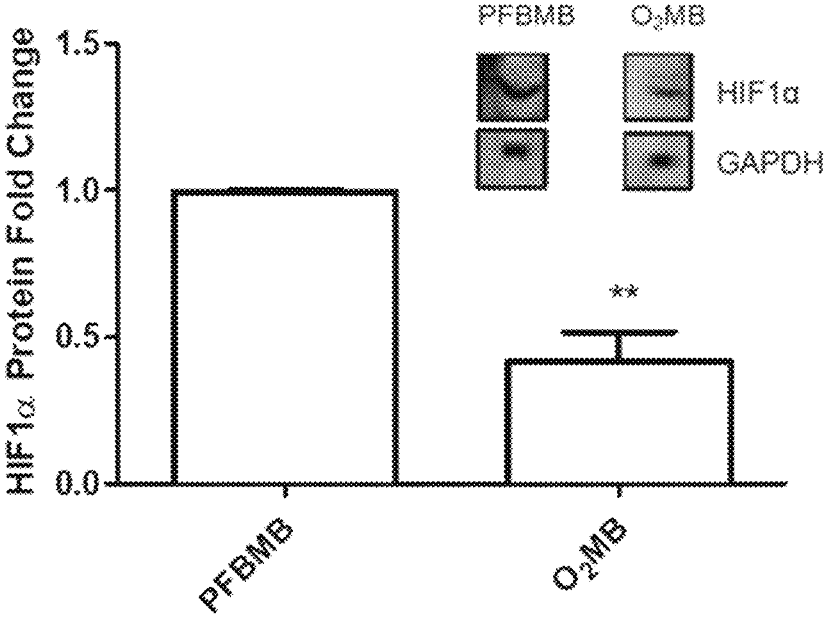

FIG. 12 shows (a) Representative fluorescence images of nude mice bearing ectopic BxPC-3 tumours before (t=0), 5 min after (t=5) and 30 min after (t=30) intravenous administration of the MB-9 conjugate with (+US) or without (−US) ultrasound applied to the tumour during IV injection. (b) Plot of % increase in tumour fluorescence recorded 5 and 30 min after intravenous administration of MB-9 conjugates with (US) or without (control) ultrasound applied to the tumour during IV injection. Increase in intensity measured relative to tumours before treatment. Error bars represent+SEM where n=3. (c) Densitometry data (compared to loading control GAPDH) showing tumour Hif1α protein expression for mice treated with an IV suspension of $O_2$MB or PFBMB. Inset shows a representative Western Blot image of HIF1α protein expression in tumours treated with an IV suspension of $O_2$MB or PFBMB. Error bars represent+SEM where n=3. * $p<0.05$,  $p<0.01$ and * $p<0.001$.

Figure 13:
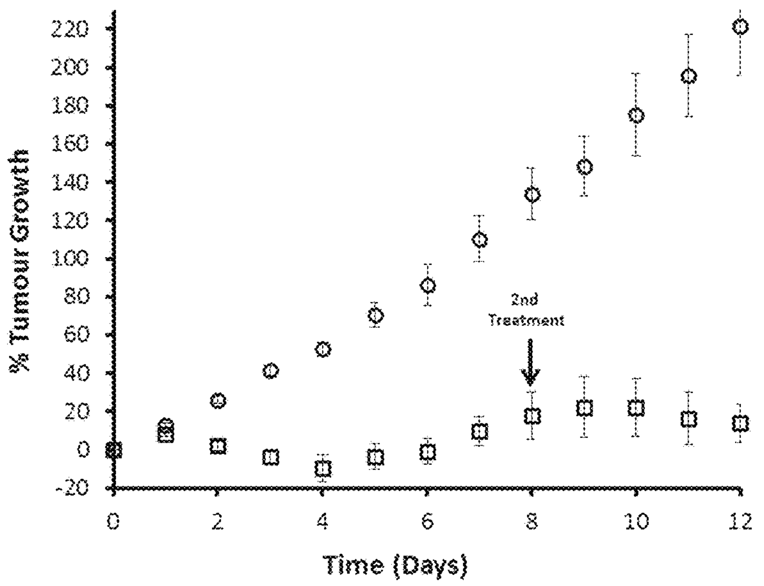

FIG. 13 shows a plot of % tumour growth versus time for mice bearing ectopic human pancreatic BxPC3 tumours treated with (i) vehicle only (open circles) or (ii) an intratumoural injection of $I_2$—IR783 (100 μL, 1 mg/kg) in a PBS:DMSO (98:2) vehicle with 780 nm light irradiation for 3×3 min with a 1 minute lag in between treatments (open squares). Mice in treatment group received a second treatment at day 8 that included 100 μL of $O_2$MBs ($1\times10^8$ MB/mL).

Figure 14:
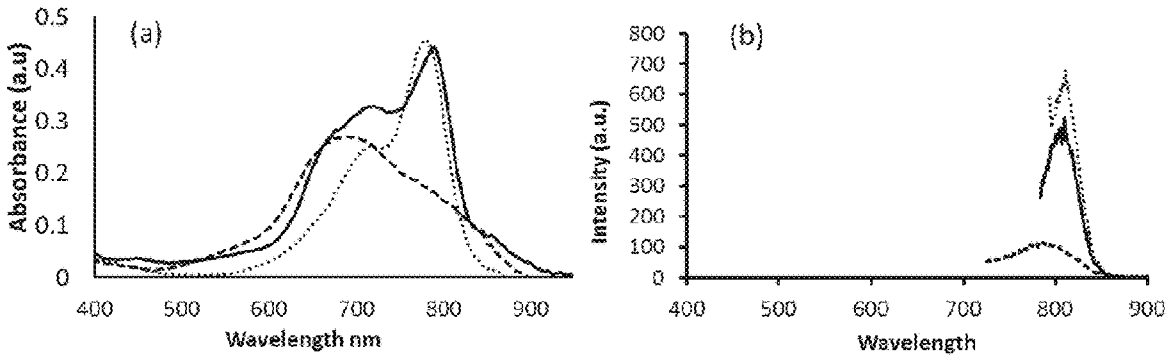

FIG. 14 shows (a) UV-Vis spectra and (b) Fluorescence spectra of ICG ( . . . ), I2-IRCYDYE (solid line) and I4-IRCYDYE (- - - ).

Figure 15:
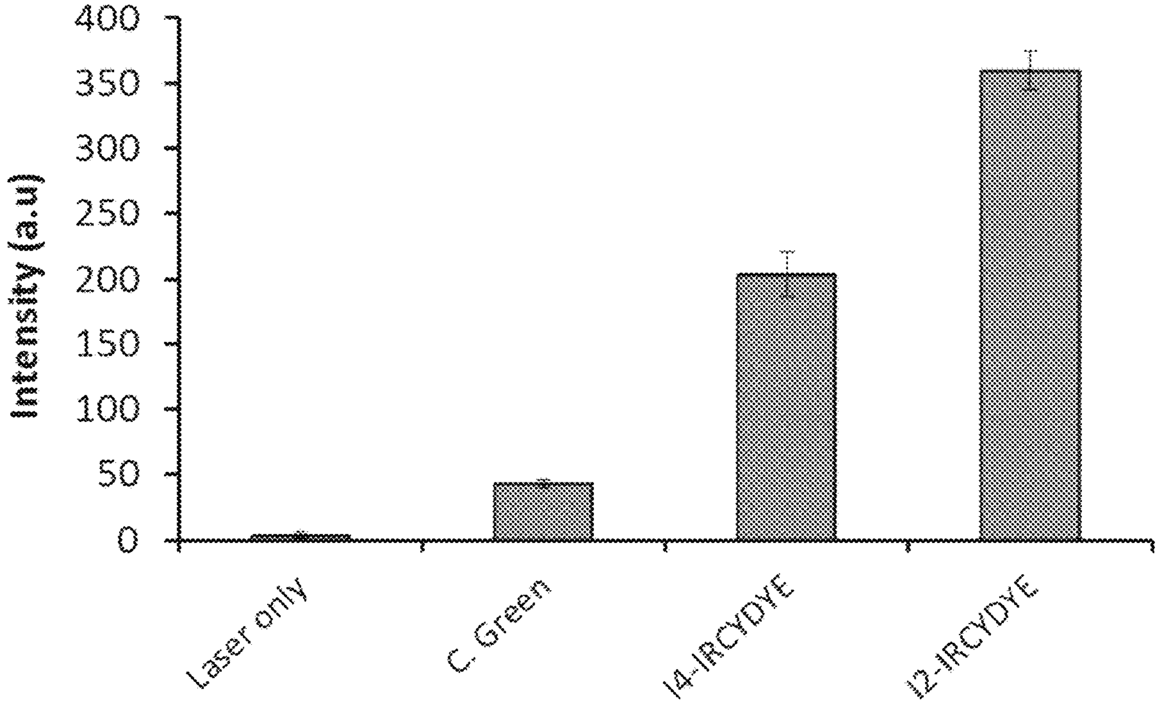

FIG. 15 shows a plot of increase in SOSG intensity at 410 nm for ICG, I2-IRCYDYE and I4-IRCYDYE. Increased SOSG intensity is indicative of singlet oxygen production.

Figure 16:
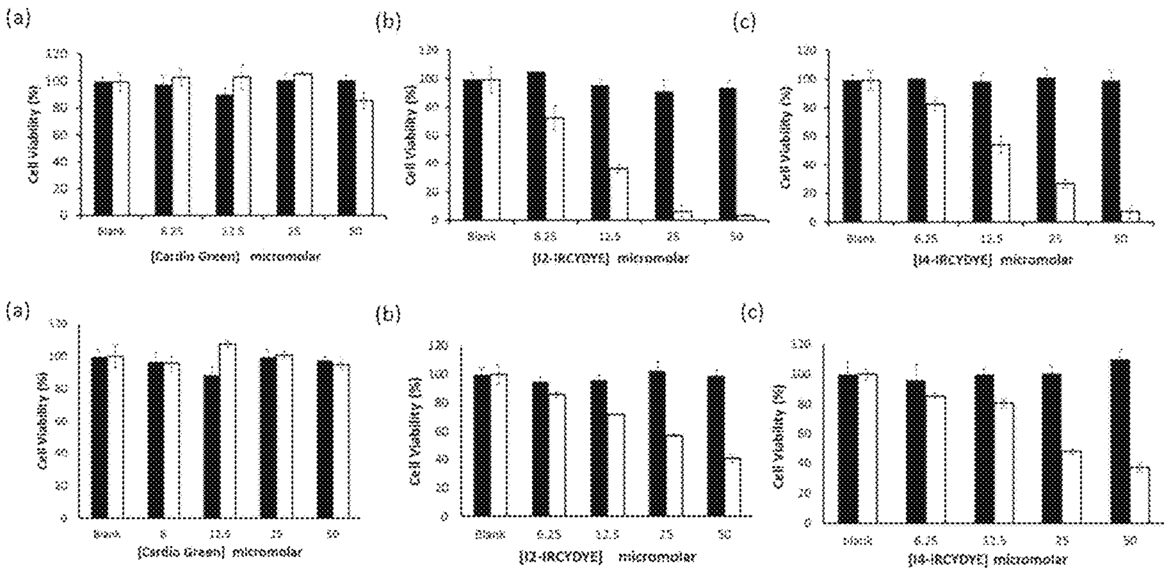

FIG. 16 shows a plot of cell viability for Mia Paca cells (upper graphs) and for BxPC3 cells (lower graphs) treated with (a) ICG, (b) I2-IRCYDYE and (c) I4-IRCYDYE with (white bars) and without (black bars) 780 nm (200 mW) light for 1 min.

Figure 17:
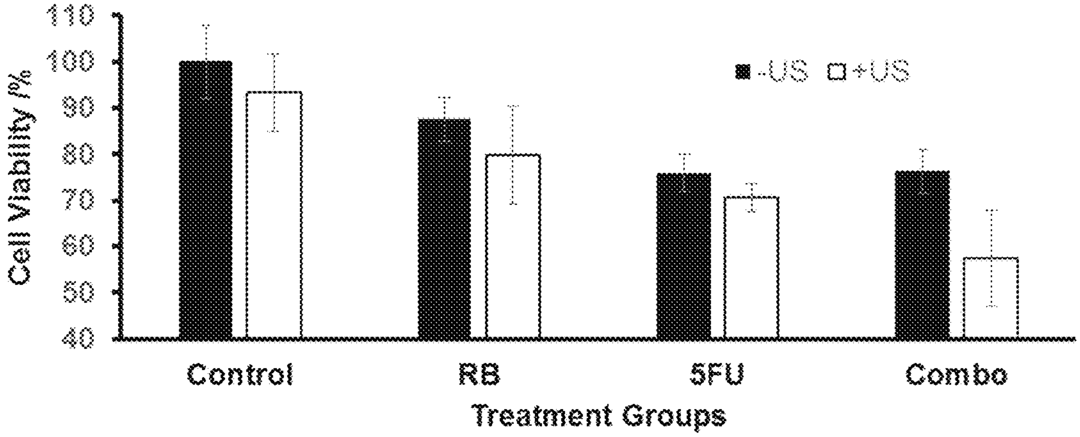

FIG. 17 shows the treatment of MiaPaCa2 cells using Rose Bengal (RB), 5-fluorouracil (5FU) and combined RB/5FU treatment±ultrasound to determine if any synergy is evident when combining SDT and 5-FU treatment. The cells were incubated with either 3 μM RB and 50 μM 5FU (or both) for 3 h as these represent sub-lethal doses and enabled synergy to be identified if evident. Ultrasound exposure was 30 sec, 3 W/$cm^2$, 1 MHz, 50% duty cycle; pulse repetition frequency of 100 MHz. Cell viability was determined 24 h following treatment using a MTT assay.

Figure 18:
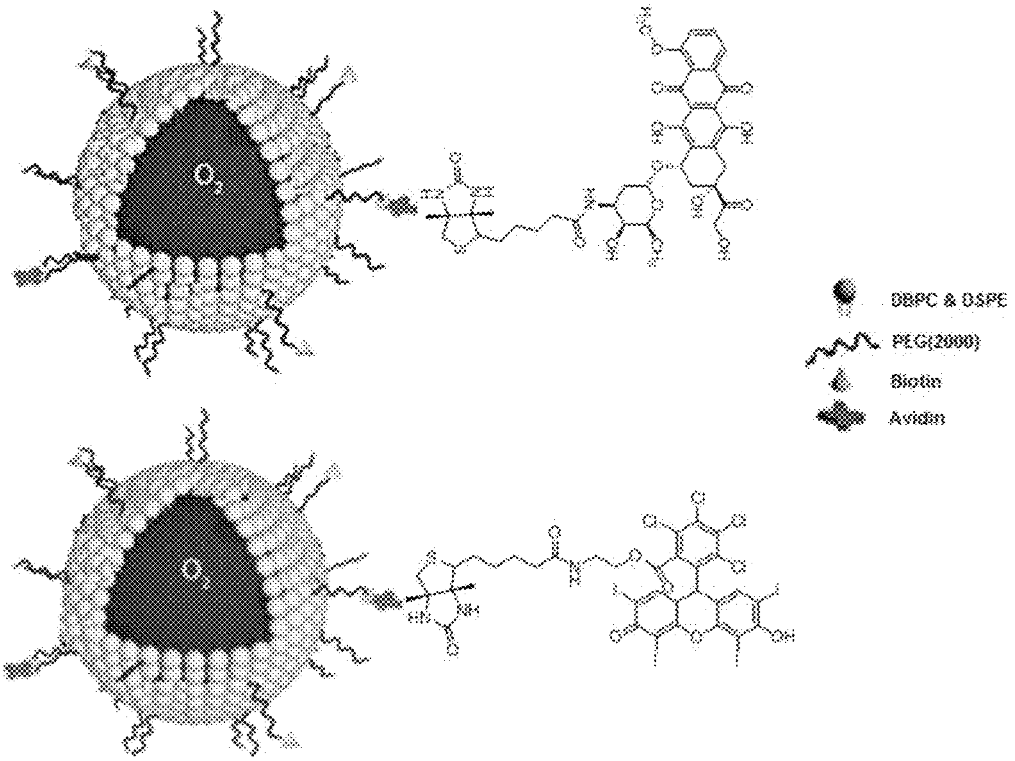

FIG. 18 shows a schematic representation of oxygen loaded microbubbles with Doxorubicin (Dox-$O_2$MB) and Rose Bengal (RB$O_2$MB) attached to the surface.

Figure 19:
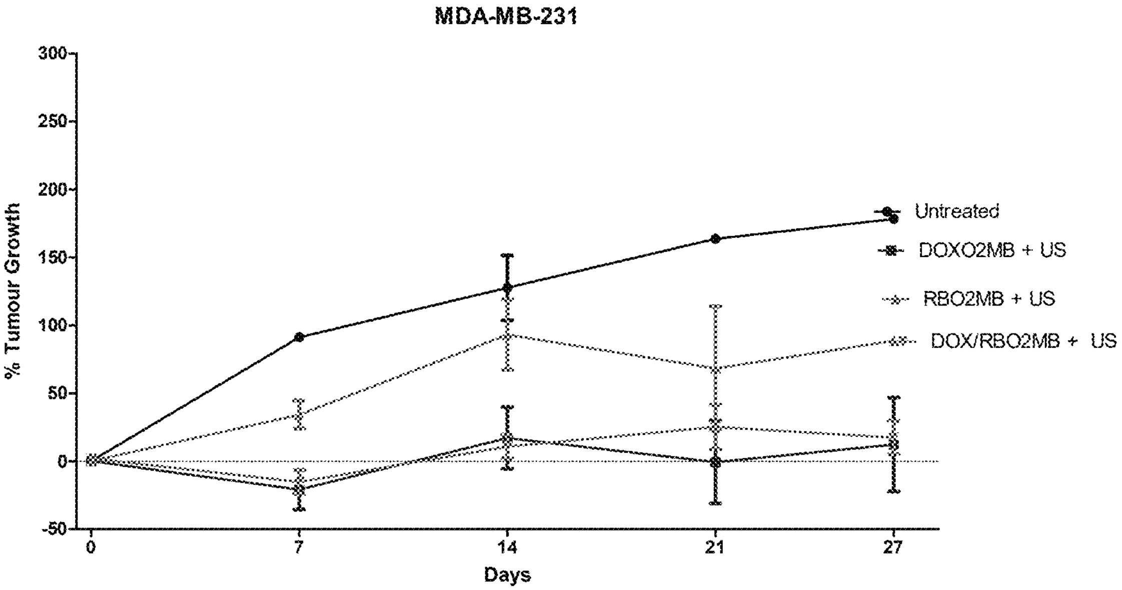

FIG. 19 shows a plot of % change in tumour volume against time for human xenograft MDA-MB-231 breast tumours treated with (i) vehicle only (ii) Dox$O_2$MB+US (iii) RB$O_2$MB+US or (iv) combined Dox$O_2$MB/RB$O_2$MB+US. A 100 μL intratumoural injection was administered on days 0 and 14 reflecting a dose of MB containing 300 μM and 475 μM of RB and DOX respectively for groups (ii) and (iii) and 150 μM and 237.5 μM of RB and DOX respectively for group (iv). Ultrasound exposure was 3.5 min, 3 W/$cm^2$, 1 MHz, 50% duty cycle; pulse repetition 100 MHz.

Figure 20:
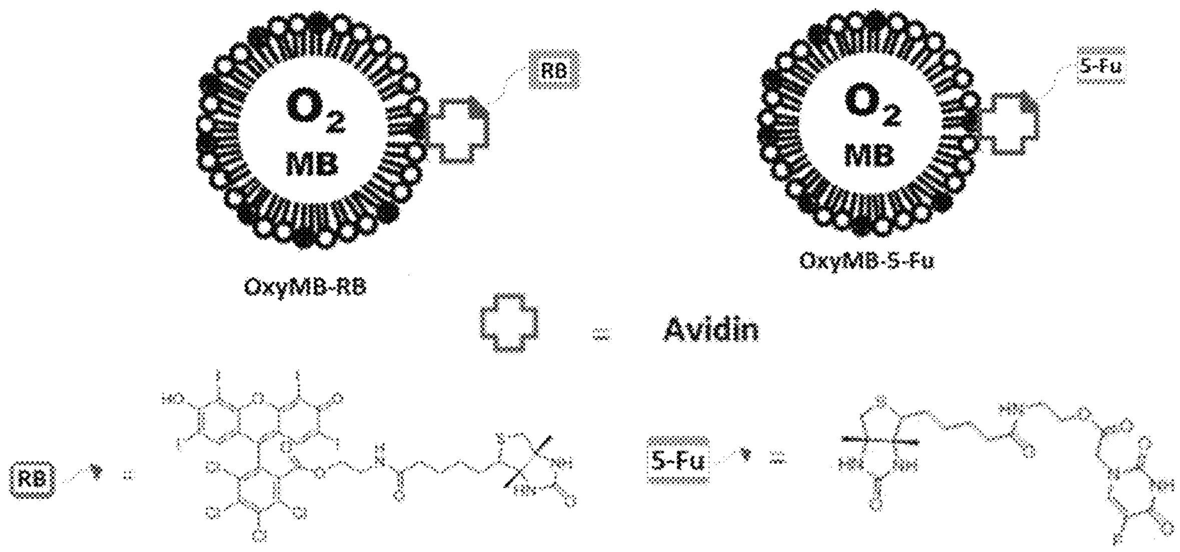

FIG. 20 shows a schematic representation for the structure of the $O_2$MB-RB and $O_2$MB-5FU conjugates.

Figure 21:
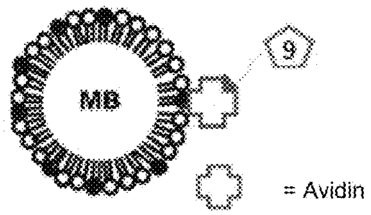

FIG. 21 shows a schematic representation of the MB-9 conjugate used in the imaging experiments.

EXAMPLES

Reagents and Equipment:

Rose bengal sodium salt, 2-bromoethylamine, NHS-biotin, MTT, avidin, FITC avidin, chloroacetic acid, 4-dimethylaminopyridine (DMAP), hydroxybenzotriazole (HOBt), N,N'-dicyclohexylcarbodiimide (DCC), anhydrous dimethylformamide (DMF) and ethanol were purchased from Sigma Aldrich (UK) at the highest grade possible. Biotin, 5-Flurouracil, di(N-succinimidyl) carbonate and 2-aminoethanol were purchased from Tokyo Chemical Industry UK Ltd. 1,2-dibehenoyl-sn-glycero-3-phosphocholine (DSPC), dibehenoylphosphatidylcholine (DBPC), 1,2-distearoyl-sn-glycero-3-phosphoethanolamine-N-[amino (polyethylene glycol)-2000 (DSPE-PEG (2000)) and DSPE-PEG (2000)-biotin were purchased from Avanti Polar Lipids (Alabaster, Alabama, USA). Doxorubicin was purchased from XABC (China). Oxygen gas was purchased from BOC Industrial Gases UK, while perfluorobutane (PFB) gas was purchased from Apollo Scientific Ltd. Phosphate Buffered Saline (PBS) was purchased from Gibco, Life Technologies, UK.

NMR spectra were recorded on a Varian 500 MHz spectrometer. ESI-MS characterisation was achieved using a LCQTM quadrupole ion-trap mass spectrometer (Finnigan MAT, San Jose, California, USA) utilising electrospray ionisation (ESI). Optical microscope images were taken with an optical microscope (Leica DM500 optical microscope). Dissolved oxygen was measured using a Thermo Scientific Orion Star A216 bench top dissolved oxygen meter. Error was expressed as +SEM (standard error of the mean) while statistical comparisons were made using an un-paired student's t-test.

Example 1—Preparation of $O_2$ Loaded Microbubbles ($O_2$MBs)

DSPC MBs were prepared as described in McEwan et al. (J Control Release. 2015; 203, 51-6). However, to improve both the physical stability of the MBs and also their stability with respect to $O_2$ retention, we utilised the longer chain lipid dibehenoylphosphatidylcholine (DBPC) in place of distearoylphosphatidylcholine (DSPC) as this has been shown in previous work to reduce the diffusivity of the MB surface and hence improve stability.

For the preparation of DBPC MBs, DBPC (4.0 mg, 4.43 μmol), DSPE-PEG (2000) (1.35 mg, 0.481 μmol) and DSPE-PEG (2000)-biotin (1.45 mg, 0.481 μmol) in a molar ratio of 82:9:9 were dissolved in chloroform and placed in a glass vial. The solution was heated at 40° C. until all the chloroform had evaporated. PBS (pH 7.4±0.1) (5 ml) was added to the dried lipid film and the contents heated above the lipid phase transition temperature (>70° C.) under constant magnetic stirring for 30 minutes. The suspension was then sonicated with a Microson ultrasonic cell disruptor for 1.5 min (100 Watts, 22.5 kHz at power setting 4), the headspace filled with perfluorobutane (PFB) gas and the gas/liquid interface sonicated (power 19) for 20 sec producing PFBMBs. The MB suspension was cooled in an ice bath for approximately 10 minutes. An aqueous solution of avidin (50 μL, 10 mg/mL) was then added to the cooled MB suspension and stirred for a further 10 minutes. The suspension was then centrifuged (300 RPM, 10 min) and the resulting MB "cake" concentrated into 1 mL of PBS (pH 7.4±0.1). This was divided into two freeze drying vials. For the PFBMBs the vials were then crimped (sealed with a metal cap). To create oxygen filled MBs the headspace of the vial and the MB suspension was sparged under a positive pressure of oxygen gas for 2 min and the vial was then crimped. Following preparation as described above, MB samples were imaged under conventional optical microscopy to determine their size distribution and concentration. 10 μL samples were removed from each suspension and diluted in 90 μL of PBS (pH 7.4±0.1) followed by examination on a haemocytometer (Bright-Line, Hausser Scientific, Horsham, PA, USA). Images were obtained with a 40× objective lens with a Leica DM500 optical microscope. The MB size distribution and concentration were then obtained using purpose written image analysis software in Matlab (2010B, The Math Works, Natick, MA, USA).

These MBs had an average diameter of 1-2 μm with a concentration of approximately 1×109 MB/mL as determined by analysis of optical microscopy images (FIG. 3). To determine the effect that inclusion of DBPC had on MB stability, we incubated PBS dispersions of the MBs prepared with DBPC or DSPC at 37° C. and counted the number of viable MBs remaining at various time intervals. The results are shown in FIG. 4 and reveal a significant improvement in stability for MBs prepared from DBPC compared with those prepared using DSPC. Indeed, after three hours incubation, 80% of DBPC MBs remained while the number of DSPC MBs reduced to 54%. These results are consistent with those from previous studies which showed that increasing the acyl chain length of the lipid reduced both the mechanical flexibility of the microbubbles and surface diffusivity.

Example 2—Preparation of Biotinylated Rose Bengal and Biotinylated 5-FU

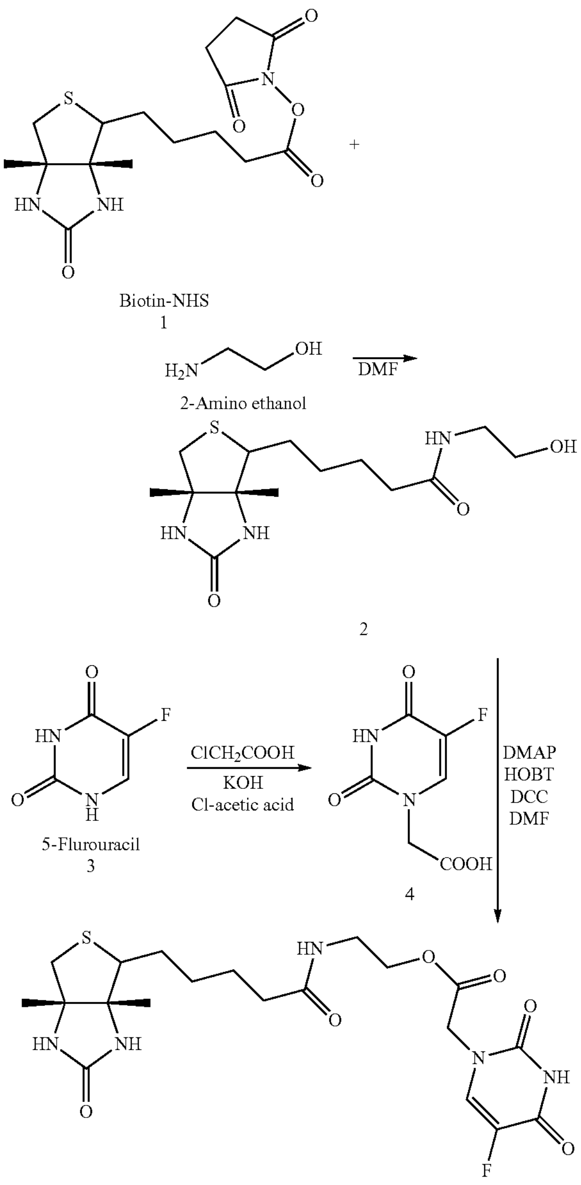

Biotin-NHS
1

2-Amino ethanol

2

5-Flurouracil
3

4

5

Scheme 1 provides a synthetic scheme for the preparation of biotin-5-FU (5). A schematic representation for the structure of the $O_2$MB-RB and $O_2$MB-5FU conjugates is provided in FIG. 20.

Biotin functionalised Rose Bengal (6) was prepared as described in McEwan et al. (J Control Release. 2015; 203, 51-6). Biotin functionalised 5-FU (5) was synthesized according to scheme 1a following the procedures outlined below.

Preparation N-(2-Hydroxyethyl)-5-(2-oxohexahydro-1H-thieno[3,4-d]imidazol-4-yl)pentanamide (2)

To an ice-cooled solution of biotin-N-hydroxysuccinimide ester (1) (prepared by the reaction between biotin and Di(N-succinimidyl) carbonate) described in Kang et al., Jr. Rapid Commun Mass Spectrom. 2009, 23 (11), 1719-1726) (3.75 g, 11 mmol) in anhydrous DMF (40 mL), was added 2-aminoethanol (1.0 ml, 16.4 mmol) and the mixture stirred at 25° C. for 30 min. The reaction was monitored by thin layer chromatography (TLC) (Merck Silica 60, HF 254, 20:80 methanol-dichloromethane v/v). The biotin-N-hydroxysuccinimide ester ($R_f$=0.76) was consumed within 15 min with the concomitant formation of the alcohol product ($R_f$=0.47). The reaction mixture was concentrated under reduced pressure and the residue co-evaporated with DMF to remove excess amounts of 2-aminoethanol. The white residue was recrystallized from water to yield 2 as a light yellow solid (1.7 g, 38%). An analytical sample was obtained from a second recrystallization, m.p. 192-195° C. $^1$HNMR (500 MHz, $D_2O$) 4.49-4.47 (m, 1H, —CH), 4.31-4.30 (m, 1H, —CH), 3.53-3.51 (m, 2H, $CH_2$), 3.23-3.18 (m, 3H, CH and $CH_2$), 2.85-2.64 (m, 2H, $CH_2$), 2.15 (t, 2H, —$CH_2$), 1.62-1.46 (m, 4H, $CH_2$ X 2), 1.32-1.26 (m, 2H, $CH_2$). $^{13}$CNMR (125 MHz, $D_2O$) 177.09 (C═O), 61.98 ($CH_2$), 60.19 (CH), 59.91 (CH), 55.24 (CH), 41.29 ($CH_2$), 39.61 ($CH_2$), 35.42 ($CH_2$), 27.77 ($CH_2$), 27.56 ($CH_2$), 25.02 ($CH_2$).

ESMS (M+$H^+$): found 288.70, calculated for $C_{12}H_{21}N_3O_3S$=287.13.

Preparation of 5-Fluorouracil-1-carboxylic acid (4)

A mixture of 5-Fluorouracil (3) (5 g, 38.4 mmol), potassium hydroxide (9.07 g, 161.6 mmol) and chloroacetic acid (3.63 g, 38.4 mmol) in 100 mL of water was refluxed for 2 h at 70° C. After cooling to room temperature, the pH of the solution was adjusted to 5.5 by the addition of concentrated hydrochloric acid. The reaction mixture was then kept in a refrigerator (5° C.) for 18 h and the resulting white crystals isolated by filtration and washed with cold water to produce 4 in 52.5% yield. mp>200° C.

$^1$HNMR (500 MHz, $D_2O$) 7.76 (d, 1H, J=6 Hz, CH), 4.29 (s, 2H, $CH_2$).

$^{13}$C NMR ($D_2O$): 173.58 (C═O), 159.97 (C═O), 150.80 (C═O), 141.20 (C), 131.74 (CH), 51.48 ($CH_2$).

ESMS (M−$H^+$): found 187.10, calculated for $C_6H_5O_4N_2F$=188.11.

Preparation of 2-(5-(2-oxohexahydro-1H-thieno[3,4-d]imidazol-4yl)pentanamido)ethyl 2-(5-fluoro-2,4-dioxo-3,4-dihydropyrimidin-1(2H)-yl)acetate (5)

N-(2-Hydroxyethyl)-5-(2-oxohexahydro-1H-thieno[3,4-d]imidazol-4-yl)pentanamide (2) (0.5 g, 1.7 mmol), 5-Fluorouracil-1-carboxylic acid (4) (0.4 g, 2.1 mmol), DMAP (0.023 g, 0.17 mmol) and HOBT (0.023 g, 0.17 mmol) were added to 20 mL of anhydrous DMF in a 100 mL 2-neck round bottom flask under a $N_2$ atmosphere. The mixture was heated at 40° C. and stirred until a homogeneous solution was obtained. DCC (0.4 g, 1.9 mmol) was then added to the reaction mixture and allowed to stir at room temperature for 12 hrs. The DMF was removed under reduced pressure, diethyl ether (50 mL) added and the contents stirred for 20 min. The resulting white semi-solid product was removed by filtration and after removing excess diethyl ether under reduced pressure, the crude product was purified by preparative HPLC (C-18 column) using acetonitrile/water (80:20 v/v) as mobile phase. The product 5 was obtained after lyophilisation of the desired fractions as a white semi-solid (0.24 g, 30% Yield).

$^1$HNMR (500 MHz, $D_2O$): 7.67 (d, 1H, J=6.0 Hz, CH), 4.50-4.47 (m, 1H, CH), 4.31-4.29 (m, 1H, CH), 4.19 (s, 2H, $CH_2$), 3.54 (t, 2H, $CH_2$), 3.22-3.19 (m, 2H, $CH_2$), 2.89-2.86 (m, 1H, CH), 2.67-2.64 (m, 2H, $CH_2$), 2.17-2.14 (m, 2H, $CH_2$), 1.61-1.47 (m, 4H, $CH_2$ X 2), 1.47-1.28 (m, 2H, $CH_2$).

$^{13}$CNMR 125 MHz, $D_2O$): 177.12 (C═O), 173.74 (C═O), 165.33 (C═O), 160.01 (C═O), 159.81 (C═O), 141.14 (C), 131.71 (CH), 62.00 ($CH_2$), 60.22 (CH), 59.94 (CH), 55.26 (CH), 51.53 ($CH_2$), 41.31 ($CH_2$), 39.64 ($CH_2$), 35.45 ($CH_2$), 27.79 ($CH_2$), 27.58 ($CH_2$), 25.14 ($CH_2$).

ESMS (M-H$^+$) found 456.20, calculated for $C_{18}H_{24}FN_5O_6S$=457.48.

Example 3—Preparation of $O_2$MB-Rose Bengal and $O_2$MB-5FU Conjugates

Saturated solutions of 5 (91.2 mM) and 6 (0.61 mM) were prepared in a 0.5% DMSO solution in PBS (pH 7.4±0.1). A 0.3 mL aliquot of these stock solutions were then added separately to two 1 mL suspensions of avidin functionalised PFBMBs (1x10$^9$ MB/mL) and the contents vortex mixed for 15 minutes. The suspensions were then centrifuged (900 rpm) for 5 min and the MB conjugates isolated as a milky suspension floating on top of the solution. The solution was removed and replaced with a further 0.3 mL of stock solution containing either 5 or 6 and the mixing/centrifugation steps repeated. The MB suspensions were then washed with PBS (5 mL), centrifuged (900 rpm) for 5 minutes and the MBs transferred to a clean centrifuge tube. This washing procedure was repeated again and the isolated PFBMB-RB and PFBMB-5FU conjugates placed in glass vial. The PFBMB-RB and PFBMB-5FU conjugates were then sparged with oxygen gas for 2 min and the resulting $O_2$MB-RB and $O_2$MB-5FU conjugates were mixed together at a ratio of 1:3.25 to produce a final suspension containing 6.8x10$^7$ MB/mL with 90.8 μM RB and 440 μM 5-FU.

This $O_2$MB-RB/$O_2$MB-5FU mix was used directly in the in vitro and in vivo experiments described herein.

Example 4—Preparation of $O_2$MB-IR820 Conjugates

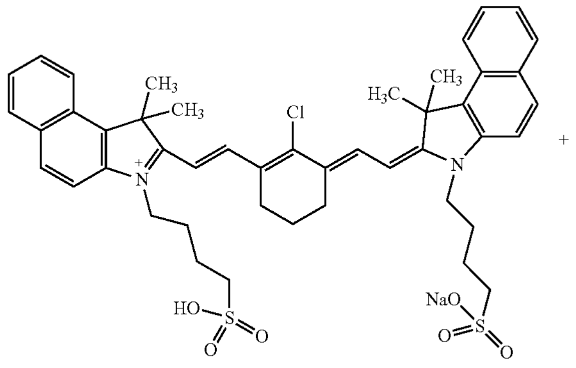

7

-continued

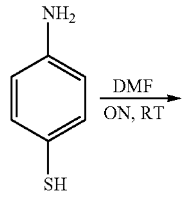

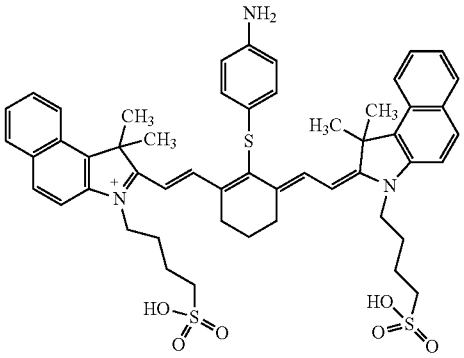

8

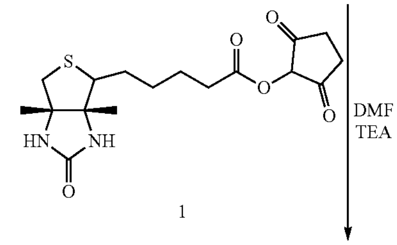

1

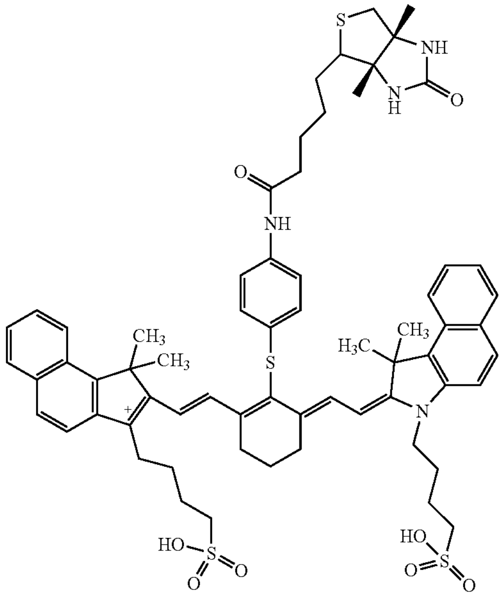

9

Scheme 2 shows the synthesis of biotin functionalised NIR absorbing dye (9). A schematic representation of the MB-9 conjugate used in the imaging experiments is provided in FIG. 21.

Synthesis of 2-((E)-2-((E)-2-((4-aminophenyl)thio)-3-((E)-2-(1,1-dimethyl-3-(4-sulfobutyl)-1H-benzo[e]indol-2 (3H)-ylidene)ethylidene)cyclohex-1-en-1-yl)vinyl)-1,1-dimethyl-3-(4-sulfobutyl)-1H-benzo[e]indol-3-ium (8)

Compound 7 was prepared following a literature procedure (James et al., Evaluation of Polymethine Dyes as Potential Probes for Near Infrared Fluorescence Imaging of Tumors: Part-1. Theranostics. 2013, 3 (9), 692-702). 4-Aminothiophenol (0.63 g, 5 mmol) was dissolved in anhydrous DMF (50 ml) under $N_2$ atmosphere. 7 (0.6 g, 0.7 mmol) was added to this solution and the mixture stirred for 18 h at room temperature. The reaction was monitored by TLC (Merck Silica 60, HF 254, using 25% MeOH/DCM as mobile phase). The DMF was removed under reduced pressure and the residue re-dissolved in DMF (5 mL) and precipitated with $Et_2O$ (15 mL). The solid product was filtered, washed with $Et_2O$ (30 mL) and purified by column chromatography (silicagel, 60-120 mesh) using MeOH-DCM (1:3) as an eluting agent. The product (230 mg, 4.8%) was isolated as reddish brown semi-solid. This compound was not stable and was used immediately in the next step. $^1H$ NMR (500 MHz, MeOH-$d_4$): 8.96-8.93 (m, 2H, Ar—CH), 8.81-8.78 (m, 2H, Ar—CH), 8.09-8.07 (m, 2H, Ar—CH), 7.90-7.89 (m, 6H, Ar—CH), 7.57-7.51 (m, 4H, Ar—CH), 7.38 (brs, 2H, $NH_2$), 7.38-7.28 (m, 2H, Ar—CH), 6.34-6.31 (m, 2H, CH X 2), 4.23 (brs, 4H, CH X 2, $CH_2$), 2.87-2.80 (m, 8H, $CH_2$ X 4), 1.98-1.91 (m, 10H, $CH_2$ X 5), 1.70 (s, 12H, $CH_3$ X 4).

$^{13}C$ NMR (125 MHz, dmso-$d_6$): 173.4, 170.2, 150.1, 148.4, 143.7, 144.6, 142.7, 134.3, 133.9, 132.4, 128.0, 126.1, 126.2, 125.5, 125.7, 117.5, 115.4, 104.7, 61.8, 59.3, 49.4, 48.9, 46.8, 30.2, 28.6, 26.8, 26.9, 25.2, 21.0.

ESMS calculated for $C_{52}H_{58}N_3O_6S_3Na_2{}^+$=961.1, found 960.3.

Synthesis of 2-((E)-2-((E)-3-((E)-2-(1,1-dimethyl-3-(4-sulfobutyl)-1H-benzo[e]indol-2 (3H)-ylidene)ethylidene)-2-((4-(5-(2-oxohexahydro-1H-thieno[3,4-d]imidazol-4-yl) penta namido)phenyl)thio)cyclohex-1-en-1-yl) vinyl)-1,1-dimethyl-3-(4-sulfobutyl)-1H-benzo[e]indol-3-ium (9)

Compound 8 (100 mg, 0.1 mmol) was added to a stirring solution of 1 (40.9 mg, 0.12 mmol) in anhydrous DMF (50 mL) to which a catalytic amount of triethylamine was added. The solution was stirred at room temperature for 5 h. The reaction mixture was added to ether (100 ml) and the contents stirred for 30 min. The precipitate was collected by filtration and purified by preparative TLC using MeOH:DCM (1:4) as eluting agent and the product isolated as a green powder. Yield=21 mg, 18.4%.

$^1H$ NMR (500 MHz, MeOH-$d_4$): 8.77 (d, J=7.8 Hz, 2H, Ar—CH), 8.21 (d, J=7.5 Hz, 2H, Ar—CH), 8.03-7.99 (m, 2H, Ar—CH), 7.73 (d, J=7.5 Hz, 2H, Ar—CH), 7.60-7.57 (m, 2H, Ar—CH), 7.47-7.44 (m, 2H, Ar—CH), 7.20-7.17 (m, 2H, Ar—CH), 7.16 (d, J=12 Hz, 1H, CH), 6.89-6.83 (m, 2H, Ar—CH), 6.58 (d, J=12 Hz, 1H, CH), 6.42 (brs, 1H, NH), 6.36 (brs, 2H, NH X 2), 4.29-4.27 (m, 6H, CH X 2, $NCH_2$), 4.10 (brs, 2H, —$CH_2$), 3.14-3.06 (m, 3H, CH, $CH_2$), 2.80-2.74 (m, 4H, $CH_2$ X 2), 2.57-2.48 (m, 4H, $CH_2$ X 2), 2.19-2.16 (m, 2H, $CH_2$), 1.88-1.59 (m, 2H, $CH_2$), 1.76 (s, 12H, $CH_3$ X 4), 1.59-1.57 (m, 2H, $CH_2$), 1.48-1.28 (m, 12H, $CH_2$ X 6).

$^{13}C$ NMR (125 MHz, dmso-$d_6$): 177.5, 174.3, 169.9, 166.2, 152.5, 150.2, 148.0, 145.3, 144.8, 140.7, 134.8, 132.6, 131.3, 130.0, 128.5, 126.3, 124.7, 120.1, 116.8, 114.8, 102.5, 64.0, 62.3, 60.1, 54.9, 50.1, 48.6, 48.1, 42.2, 36.7, 32.8, 30.2, 28.4, 28.3, 26.9, 26.0, 24.5, 22.8.

ESMS calculated for $C_{62}H_{72}N_5O_8S_4{}^+$=1142.4 (protonated form, $M^+$), found 1143.4.

Preparation of $O_2$MB-IR820 Conjugates:

Biotin functionalised IR-820 (9) was attached to the surface of $O_2$MBs following the procedure as described above for 5-FU and Rose Bengal. [MB]=$2.6\times10^8$; [9]=280 μM.

Example 5—Ultrasound Mediated $O_2$ Release from $O_2$MBs

A 0.5 mL suspension of $O_2$MBs ($1\times10^8$) prepared in Example 1 was added to degassed PBS (pH 7.4±0.1) (4.5 mL). The dissolved oxygen level of this solution was measured over a 20 min period at 2 min intervals using a dissolved oxygen meter. Ultrasound was applied after 4.5 min for Imin, using a frequency of 1 MHz, an ultrasound power density of 3.0 $Wcm^{-2}$ and a duty cycle of 50% (pulse frequency=100 Hz). Control experiments using PFBMBs were also performed following the same procedure.

Figure 5:
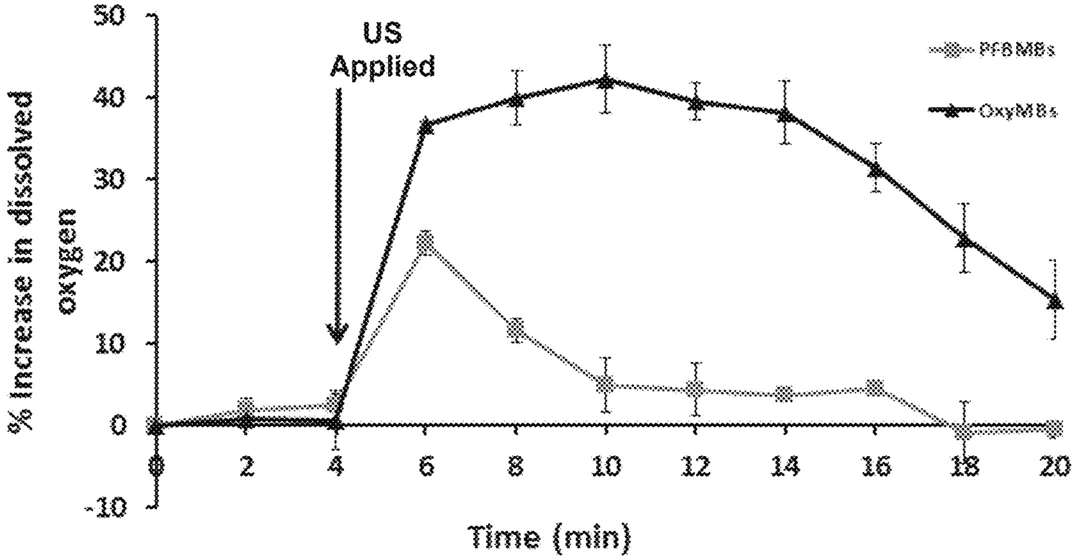

If $O_2$MBs are to be successful as carrier for oxygen delivery in vivo, it is important that gas exchange between the core of the MB and blood is minimised until the MB is exposed to ultrasound at the target site. The half-life of commercial MBs ranges from 0.97 min in men to 1.23 min in women. Therefore, it is important that $O_2$MBs can retain their oxygen for at least this time period in situations where an oxygen diffusion gradient may exist. In an attempt to simulate such a scenario, $O_2$MBs (0.5 mL, $1\times10^8$) were added to 4.5 mL of degassed PBS (pH 7.4±0.1) in a glass vial and the contents agitated periodically at 37° C. As the $O_2$MBs float at the top of the PBS solution they were in direct contact with air in the headspace of the open vial. The amount of dissolved $O_2$ in the PBS solution was determined using a dissolved oxygen meter and was measured for 4.5 min before and 14.5 min after ultrasound treatment. As a control, experiments using PFBMBs were also conducted. The results are shown in FIG. 5 and illustrate that the $O_2$MBs effectively retain their $O_2$ until destruction by the externally applied ultrasound at which point the dissolved oxygen increases by more than 40% five minutes after irradiation. In contrast, the dissolved oxygen in the PFBMB control experiment increased by about 20% 1 min after exposure to ultrasound and then decreased to only 5% at five minutes after exposure to ultrasound. We believe this initial increase in dissolved $O_2$ in the control preparation was due to ultrasound-mediated agitation of the fluid in the measurement chamber. Nevertheless, the results suggest that the $O_2$MBs effectively retain oxygen and exposure to ultrasound results in an increase in dissolved oxygen that is sustained for a relatively prolonged period of time in this system. We believe this time frame of both retention and ultrasound-mediated release would facilitate sufficient time to enable targeting of microbubbles and their gas payload to a specific anatomical site and provide an increase in dissolved oxygen in a tissue microenvironment that would be sufficient to support enhanced ROS generation during SDT.

Example 6—In Vitro Cytotoxicity Experiments

Human primary pancreatic adenocarcinoma cell lines MIA PaCa-2 and PANC-1 were maintained in Dulbecco's Modified Eagle's Medium while BxPC-3 cells were maintained in RPMI-1640 medium, all of which were supplemented with 10% (v/v) foetal bovine serum in a humidified 5% $CO_2$ atmosphere at 37° C. These cell lines were plated into the wells of a 96-well plate at a concentration of $5\times10^3$ cells per well and incubated for 21 h at 37° C. in a humidified 5% $CO_2$ atmosphere before being transferred to a hypoxic chamber at 37° C. ($O_2/CO_2/N_2$, 0.1:5:94.9 v/v/v) for 3 h (this is intended to mimic the hypoxic conditions found at a tumor site). The medium was then removed from each well and replaced with $O_2$MB-RB (50 µL, 5 µM RB) and $O_2$MB-5FU (50 µL, 100 µM 5FU) conjugates. Individual wells were then treated with ultrasound delivered using a Sonidel SP100 sonoporator (30 sec, frequency=1 MHz, ultrasound power density=3.0 $Wcm^{-2}$, duty cycle=50% with pulse repetition frequency=100 Hz). Cells were kept in the hypoxic environment for a further 3 hours before the treatment solution was removed, the cells washed with PBS and fresh media added (200 µL per well). Plates were then incubated in normoxic conditions (i.e. humidified 5% $CO_2$ atmosphere at 37° C.) for a further 21 hours before cell viability was determined using a MTT assay (McHale et al., Cancer Lett 1988; 41, 315-21). A similar procedure was repeated for the vehicle only, gemcitabine (drug approved for use in pancreatic cancer treatment), 5-FU, $O_2$MB-5FU+US, $O_2$MB-RB+US and the $O_2$MB-RB/$O_2$MB-5FU mix-US. In all experiments the amount of RB, 5-FU and gemcitabine used was 5 µM, 100 UM and 100 µM respectively. All groups were also repeated using PFBMB conjugates with the same amount of RB or 5-FU attached.

The results, shown in FIG. 6, reveal that a statistically significant reduction in viability was observed in all three cell lines for cells treated with the combined SDT/antimetabolite therapy (i.e. $O_2$MB-RB/$O_2$MB-5FU mix+US) compared to that of cells treated with either antimetabolite therapy alone (i.e. 5-FU or gemcitabine). Indeed, a statistically significant reduction in viability was also observed for cells treated with the combined therapy relative to that of cells treated with SDT treatment alone (i.e. $O_2$MB-RB+US). That the SDT effect observed in such hypoxic conditions is greatly enhanced through the use of $O_2$MBs was confirmed by comparing the difference in the cytotoxicity between the $O_2$MB-RB/$O_2$MB-5FU mix with ultrasound treatment and an otherwise identical mix of PFBMB conjugates with ultrasound treatment (FIG. 7). Indeed, statistically significant ($p<0.01$) reductions in cell viability of over 20% were observed for all three cell lines treated with the $O_2$MB conjugates compared to the PFBMB conjugates. Collectively, the results shown in FIGS. 6 and 7 clearly highlight the benefit gained when SDT is combined with antimetabolite therapy, particularly in hypoxic environments where $O_2$MBs can provide additional $O_2$ to improve the SDT effect.

Example 7—In Vivo Cytotoxicity Experiments

BxPc-3 cells were maintained in RPMI-1640 medium supplemented with 10% foetal calf serum as described above. Cells ($1\times10^6$) were re-suspended in 100 µL of Matrigel® and implanted into the rear dorsum of female Balb/c SCID (C.B-17/IcrHan®Hsd-Prkdcscid) mice. Tumour formation occurred approximately 2 weeks after implantation and tumour measurements were taken every other day using calipers. Once the tumours had reached an average volume of 218 $mm^3$, calculated from the geometric mean diameter using the equation tumour volume=$4\pi R^3/3$, animals were randomly distributed into 10 groups (n=4). Following induction of anaesthesia (intraperitoneal injection of Hypnorm/Hypnovel), a 100 µL mixture of PBS containing 02 MB-RB (MB=$1.6\times10^7$, [RB]=90.8 µM) and $O_2$MB-5FU (MB=$5.2\times10^7$, [5FU]=440 µM) was injected directly into each tumour. Intratumoural injection was chosen as the route of administration to preclude experimental variation resulting from pharmacokinetic behaviour of the platform. Where appropriate, tumours were then treated with ultrasound for 3.5 min at an ultrasound frequency of 1 MHz, an ultrasound power density of 3.5 $Wcm^{-2}$ ($I_{SATP}$; spatial average temporal peak) and using a duty cycle of 30% at a pulse repetition frequency of 100 Hz. Additional treatment groups included (i) no drug; (ii) $O_2$MB-RB conjugate alone #ultrasound treatment; and (iii) $O_2$MB-5FU conjugate alone #ultrasound treatment. Gemcitabine (440 µM) and 5-FU (440 µM) only treatments were also performed. After treatment, animals were allowed to recover from anaesthesia and tumour volume and body weight were recorded daily for nine days. The % increase in tumour volume was calculated employing the pre-treatment measurements for each group.

The tumour volume was measured daily for 9 days and the % change in tumour volume for each group plotted as a function of time. For ease of interpretation, only results from six of the ten groups are shown in FIG. 8*a*. These results reveal a dramatic reduction in tumour volume for mice treated with the combined SDT/antimetabolite therapy compared to either gemcitabine or 5-FU treatment alone. Indeed, 9 days after treatment, tumours in mice treated with gemcitabine or 5-FU alone grew by 125.1 and 123.3% respectively, while tumours treated with the $O_2$MB-RB/$O_2$MB-5FU mix+US grew by only 29.1% over their original starting volume within the same time period. In addition, there was also a statistically significant reduction in tumour volume for tumours treated with the combined SDT/5-FU therapy (i.e. $O_2$MB-RB/$O_2$MB-5FU mix+US) relative to SDT treatment alone (i.e. $O_2$MB-RB+US) with tumours being on average 30.2% smaller 9 days after treatment. Analysis of the average body weight (FIG. 8*b*) for animals in each of the groups showed no noticeable reductions over the course of the experiment suggesting the treatments did not produce any acute adverse effects.

In these experiments, gemcitabine was administered as an intra-tumoral injection at a concentration of 0.264 mg/kg in order to provide a direct molar comparison with the amount of 5-FU used (440 µM). Even though this amount was delivered directly to the tumour it is significantly less than the normal systemic dose of gemcitabine (120 mg/kg) used in mice.

In order to compare the effectiveness of the combined SDT/5-FU therapy against systemic gemcitabine therapy, we treated mice bearing ectopic BxPC-3 tumours with gemcitabine (120 mg/kg) administered by intraperitoneal (IP) injection on days 0, 3 and 8. Tumour volume was measured daily as before and compared to untreated animal controls. These results (FIG. 9) demonstrate that while the tumour volume in the control group increased by about 100%, tumour volume increased by 38% in the gemcitabine treated group and at no point in the therapy did the tumour volume decrease below the starting tumour volume. In contrast, with a single treatment, for the combined SDT/5FU therapy (FIG. 8) the tumour volume decreased below the initial treatment volume and remained so up to 6 days post treatment while tumours in the gemcitabine group exhibited a 20% increase in tumour volume at day 6. That such dramatic response can be achieved using relatively low amounts of sensitiser/5-FU and following a single treatment is extremely promising and suggests the targeted delivery of such agents could provide enhanced therapeutic benefit with reduced side effects.

Example 8—In Vivo NIR Fluorescence Imaging of $O_2$MB-9 Conjugates Following IV Administration to Tumour Bearing Mice Athymic nude mice were anaesthetised (intraperitoneal injection of Hypnorm/Hypnovel) and the $O_2$MB-9 conjugate (100 μL) was administered via tail vein injection. In the treatment group, ultrasound (conditions as in 2.10 above) was applied to the tumours during and for 3 minutes after IV injection while no ultrasound was applied to the tumours in the control group (n=3 in each group). Following administration (at t=5 min and t=10 min), animals were placed in the chamber of a Xenogen IVIS® Lumina imaging system on fluorescence mode using the ICG filter set (excitation: 705-780 nm; emission: 810-885 nm). Data were captured and analyzed using the Living Image® software package version 2.60. Quantitative data were obtained by drawing a region of interest around the tumour and comparing the fluorescent signal (photons/second) at t=5 and t=10 min post $O_2$MB-9 administration with the fluorescent signal obtained prior to administration.

Example 9—Immunohistochemistry and qRT-PCR Analysis

We were also interested in probing the effects of combined SDT/5-FU treatment at the molecular level when compared to 5-FU treatment alone. In order to do this, tumours in the control group (i.e. no treatment), the $O_2$MB-5FU+US group (i.e. 5-FU), and $O_2$MB-RB/$O_2$MB-5FU mix+US group (i.e. combined treatment) were harvested at the end of the monitoring period and subjected to immunohistochemistry and qRT-PCR analysis.

HIF1α Expression in the Tumour Post IV Administration of $O_2$MB:

Athymic nude mice were anaesthetised (intraperitoneal injection of Hypnorm/Hypnovel) and either PFBMBs or $O_2$MBs (100 μL) were administered via tail vein injection (n=3 in each group). Ultrasound (conditions as in 2.10 above) was applied to the tumour during and for 3 minutes after IV injection and the tumours were excised 30 minutes later. For Western blotting analysis of HIF-1α protein expression, total protein was extracted using urea buffer. Primary murine antibodies employed in these studies were anti-HIF1α (Millipore, 1:500), and anti-GAPDH (Sigma, 1:1000). Protein samples were electrophoresed on a 4-12% TruPAGE® gel and transferred to nitrocellulose membranes. Blocking of non-specific binding was carried out in 5% (w/v) bovine serum albumin diluted in 1× tris buffered saline containing 0.05% (v/v) Tween 20. Membranes were then incubated in the appropriate secondary antibody, goat anti-mouse IgG-HRP (1:10000 of the stock solution). Secondary antibodies were purchased from Santa Cruz Biotechnology, Heidelberg, Germany. Densitometry was carried out to quantify HIF1α protein expression using GAPDH as a housekeeping reference.

Immune Response Characterisation:

To characterise the immune response in tissues subjected to therapy, Bcl3 and Bcl2 protein expression was examined using immunohistochemistry in tissue samples harvested at the end of the monitoring period. Immunohistochemical (IHC) evaluation for Bcl2 and Bcl3 proteins was performed on paraffin-embedded sections. The paraffin-embedded tissue samples were cut to a 4 μm thickness using a Leica RM2235 microtome (Leica Biosystems Ltd., Newcastle) and examined on a coated glass slide. IHC analysis for Bcl2 (clone: BCL-2/100/D5) and Bcl3 (clone: 1E8) were diluted 1:200 and 1:150 respectively. Both antibodies were mouse anti-human obtained from Leica Biosystems. Immunostaining was carried out using the automated Bond-Max system (Leica Biosystems Ltd., Newcastle) using on board heat-induced antigen retrieval with Bond Epitope Retrieval Solution 2 (EDTA based on pH 9.0) for 30 min. Endogenous peroxidase activity was blocked using 0.3% hydrogen peroxide for 5 min. The histological specimens were incubated with the primary antibody for 15 min at room temperature and the slides were incubated with rabbit anti-mouse for 8 min at room temperature. The slides were then incubated with goat anti-rabbit polymer reagent for 8 min at room temperature. The reactions were developed using a bond polymer refine detection kit and followed by colour development with 3,3'-diaminobenzidine tetrahydrochloride as a chromogen for 10 min. The immunohistochemistry intensity and proportion scores were carried out according to Allred et al. (Prognostic and predictive factors in breast cancer by immunohistochemical analysis. 1998, 11 (2): 155-68). In order to confirm immunohistochemical studies Bcl3 expression was also examined at the transcriptional level. mRNA expression of Bcl3 was measured with gene specific qRT-PCR using the primers listed in Table 1:

TABLE 1

Primers used in qRT-PCR.

| Primer | Sequence |
|---|---|
| Bcl3 Forward [Seq ID No 1] | CCTTTGATGCCCATTTACTCTA |
| Bcl3_Reverse [Seq ID No 2] | AGCGGCTATGTTATTCTGGAC |
| β-Actin Forward [Seq ID No 3] | CGTGGGCCGCCCTAGGCACCA |
| β-Actin Reverse [Seq ID No 4] | TTGGCCTTAGGGTTCAGGGGGG |
| 18SrRNA_Forward [Seq ID No 5] | TGACTCAACACGGGAAACC |
| 18SrRNA_Reverse [Seq ID No 6] | TCGCTCCACCAACTAAGAAC |

qRT-PCR and analysis were performed following previously published protocols (Hamoudi et al., Leukemia, 2010, vol. 24, no. 8, pp. 1487-1497; and Bi et al., Haematologica, 2012, 97, 926-930). Briefly, RNA was extracted from micro-dissected slides using the RecoverAll Kit (Life Technologies, Paisley, UK). cDNA synthesis was carried out using the Superscript III First Strand cDNA synthesis kit (Life Technologies, Paisley, UK) using the reverse primer of each of the genes including the two housekeeping genes; 18S rRNA and β-actin. qRT-PCR was carried out using the SYBR Green kit on the CFX96 instrument (BioRad, UK). The qRT-PCR cycle was as follows: 95° C. for 3 minutes, 95° C. for 10 seconds, 60° C. for 45 seconds for 40 cycles. For analysis, the geometric mean of 18S rRNA and β-actin was taken as the single housekeeping value. Statistical comparison between the groups was carried out using two-way ANOVA with Bonferroni post-hoc analysis.

Results:

The immunohistochemistry results revealed that at the protein level, there was Bcl3 and Bcl2 deregulation between both treatment groups and the control group. At this level of analysis, Bcl3 intensity and proportion were higher in the control and 5FU groups but decreased in the combined treatment group. Similarly, Bcl2 protein expression was highest in the control group, decreased in the SFU group and was undetectable in the combined treatment group (FIG. 10). At the mRNA level, a similar pattern was observed for Bcl3 (FIGS. 11*a* and 11*b*) with the ΔΔCt showing significant decreases of approximately 5- and 7-fold for the 5FU and combined treatment groups respectively relative to the control group ($p<0.001$). Bcl3 is a key member of the NF-κB pathway and is involved in regulating many cellular pathways including survival, proliferation, inflammation and immune response. Bcl3 expression and activation has been associated with increased cellular proliferation or survival, dependent on the tissue and the type of stimuli. Its transcriptional repressor function has been shown to be involved in regulating immune responses as well as the development and activation of immune cells (Wessells et al., J Biol Chem 2004; 279:49995-50003, and Kuwata et al., Blood 2003; 102:4123-4129). The fact that Bcl3 expression was deregulated suggests an alteration in the immune response as well as survival and proliferation cell signalling. This was confirmed by the fact that Bcl2, which is an important anti-apoptotic gene, was higher in the control but its expression decreased remarkably after the combined treatment. Indeed Bcl2 expression is known to be up-regulated in the majority of primary pancreatic tumours (Campani et al., Pathol. 2001, 194 (4), 444-450) and it has been demonstrated that using Bcl2-specific siRNA to down-regulate its expression has anti-proliferative and pro-apoptotic effects on pancreatic tumour growth in vitro and in vivo (Ocker et al., Gut, 2005, 54 (9), 1298-1308). More recently, it has been shown that a G-quadruplex-binding compound (MM41) that exhibits anti-tumour activity using the MIA PaCa-2 pancreatic cancer xenograft model, reduced Bcl2 levels by 40% following analysis at the protein level (Ohnmacht et al., Sci Rep. 2015, 16 (5): 11385). Taken together, these results indicate a marked effect on cellular signalling pathways as a result of the combined SDT/5-FU treatment and suggest that SDT could provide significant therapeutic benefit for pancreatic cancer patients when employed together with conventional chemotherapy-based regimes.

Example 10—NIR Imaging

To be suitable for clinical translation, the MB suspension will need to be administered intravenously and the MBs disrupted at the tumour site using appropriate ultrasound conditions. Such a strategy should enhance localisation of the sensitiser/chemotherapeutic and increase tumour $pO_2$ at the tumour site. To test the feasibility of such an approach the biotin functionalised near infrared absorbing cyanine dye (9) was employed as a surrogate for RB and 5-FU (Scheme 2)-see Example 4. The UV-Vis and fluorescence spectra of 9 reveal absorbance (750 nm) and emission maxima (818 nm) in the NIR region making this compound ideal for in vivo imaging.

As described in Example 4, dye (9) was loaded onto the MB surface following the same procedure used for RB and 5-FU. The $O_2$MB-9 conjugate was then administered intravenously via the tail vein of athymic nude mice bearing ectopic Bx-PC3 tumours. Ultrasound was applied directly to the tumour during and for 3 minutes after IV administration. Control experiments in the absence of ultrasound were used for comparative purposes. The mice were imaged before, 5 and 30 minutes after administration using an IVIS whole body imaging system. Representative images (FIG. 12*a*) reveal strong tumour fluorescence 30 min after treatment for mice in the ultrasound treated group while mice in the control group showed negligible tumour fluorescence, with most of the emission observed from the liver region. When the intensity of tumour fluorescence was measured relative to the pre-treatment value (FIG. 12*b*), a statistically significant 7-fold enhancement was observed for the ultrasound treated group relative to the control group, 30 min following treatment ($p<0.01$). Furthermore, when either $O_2$MB or PFBMB were administered to tumour-bearing animals by tail vein injection and subsequently treated with ultrasound, protein extracts from surgically-excised tumours revealed a significant decrease in Hif-1α in tumours treated with the $O_2$MB (FIG. 12*c*). These results suggest that the application of ultrasound to the tumour, during and immediately after administration of the $O_2$MB-9 conjugate, facilitates stimulus-dependant destruction of the MBs in the tumour vasculature which in turn facilitates release of both $O_2$ and the attached payload in a targeted manner. The end result is an increase in tumour $pO_2$ as evidenced by reduced expression of Hif1α protein and a greater concentration of drug in the tumour as evidenced by the enhanced fluorescence of (9).

Example 11—Monoiodo ICG Synthesis ($I_2$—IR783 or "I2-IRCYDYE")

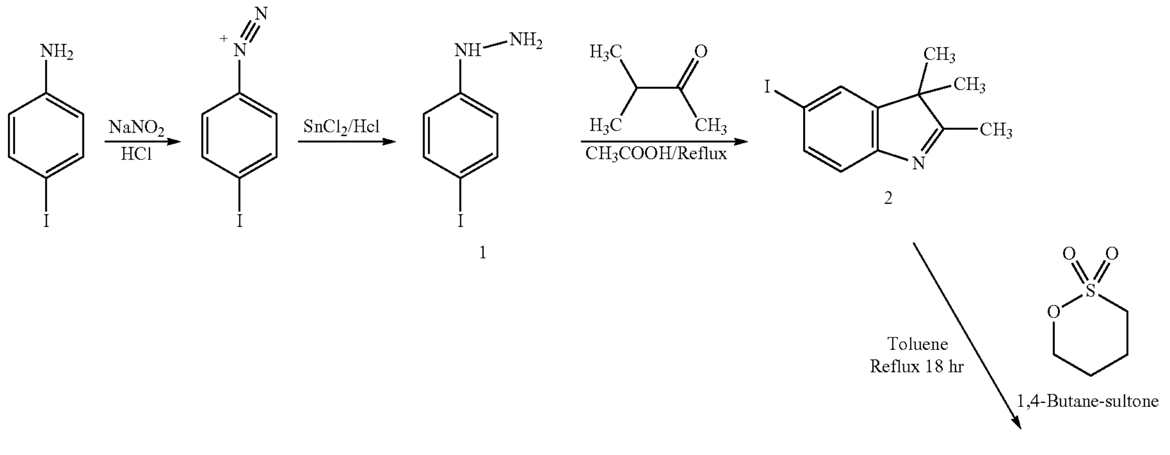

1

2

1,4-Butane-sultone

-continued

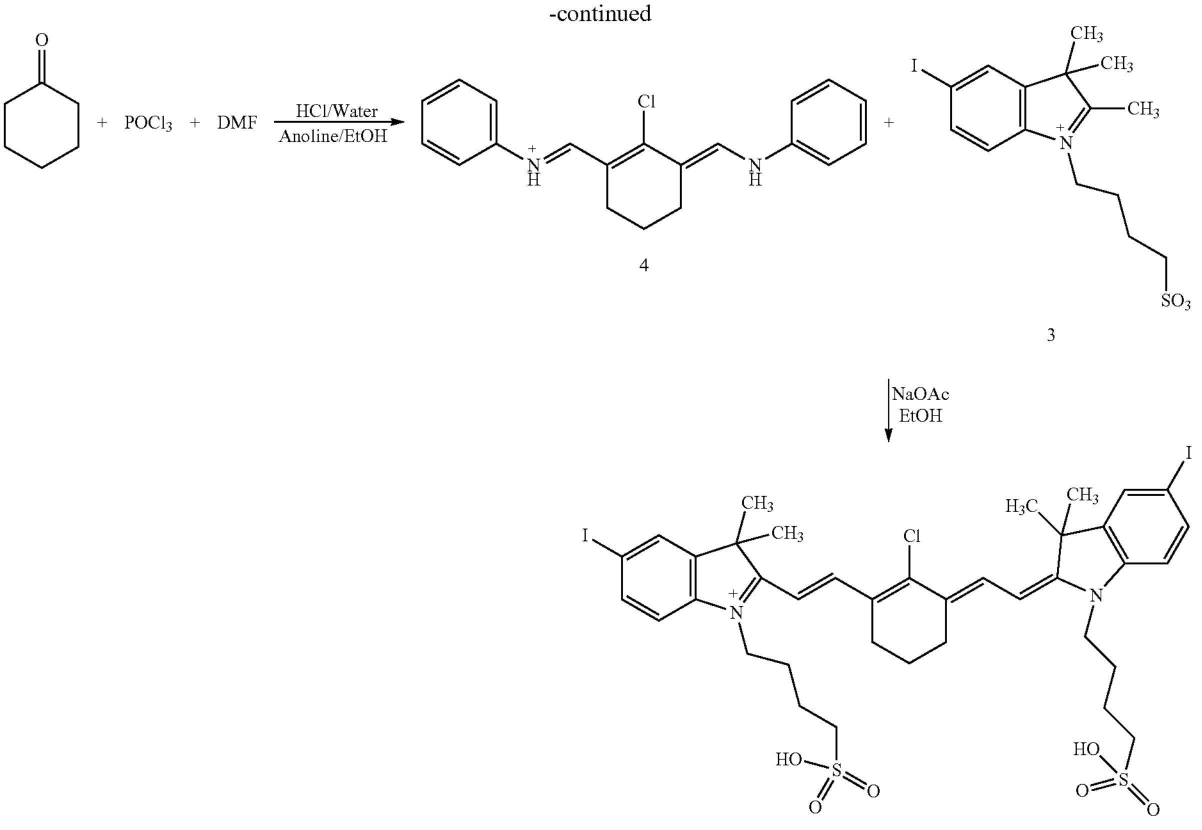

4 3 5

Synthesis of (4-iodophenyl)hydrazine (1)

20 g (91.3 mmol) of 4-iodoaniline was stirred with a solution of 15 ml concentrated hydrochloric acid and 15 ml of water. The mixture was cooled to about −10° C. and 12.6 g (182.6 mmol) of $NaNO_2$ in 45 ml of water was added drop wise with continuous stirring. The suspension was allowed to stir for another 30 minutes and then an ice cold solution of $SnCl_2·2H_2O$ (67.99 g, 301.3 mmol in 40 ml of concentrated HCl) was added drop wise keeping the temperature at −10° C. The reaction mixture was stirred at that temperature for 1.5 hr and at 5° C. overnight. The light brown precipitate obtained was filtered and washed three times with water. This solid mass thus obtained was then stirred with saturated solution of NaOH in water (100 ml) and extracted with ether (200 ml). The ether layer was washed with aqueous solution of NaOH, $Na_2S_2O_3$ and water. After drying with $MgSO_4$ (anhydrous), the ether layer was evaporated to dryness to afford 17.94 g of (4-iodophenyl) hydrazine as brown powder. m.p=104-106° C.

$^1H$ NMR ($CDCl_3$): 7.48 (d, J=8.0 Hz, 2H, Ar—CH), 6.62 (d, J=8.0 Hz, 2H, Ar—CH), 5.18 (brs, 1H, NH), 3.55 (brs, 2H, $NH_2$).

ESMS (M+H) found=235.00, calculated for $C_6H_7IN_2$=234.04.

Synthesis of 5-iodo-2,3,3-trimethyl-3H-indole (2)

12.68 g (54.1 mmol) of (4-iodophenyl) hydrazine (1) and 8 g (92.8 mmol) of 3-methyl-2-butanone were refluxed in 100 ml of glacial acetic acid for 20 hrs. The acetic was evaporated and the residue was dissolved in ether. Insoluble precipitate was filtered off, and the etheric solution was washed with aqueous solution of NaOH followed by $Na_2S_2O_3$ and water. The organic layer was dried with anhydrous $Na_2SO_4$ and the ether was removed under reduced pressure to afford 10.5 g of 5-iodo-2,3,3-trimethyl-3H-indole (2) as red gummy liquid.

$^1H$ NMR ($CDCl_3$): 7.60 (dd, J=4.5, 8.0 Hz, 2H, Ar—CH), 7.28 (d, J=8.0 Hz, 1H, Ar—CH), 2.25 (s, 3H, $CH_3$), 1.20 (s, 6H, $CH_3$ X 2).

$^{13}C$ NMR ($CDCl_3$): 153.4 (C), 148.1 (C), 139.3 (C), 136.6 (CH), 130.6 (CH), 121.8 (CH), 89.9 (C), 54.0 (C), 23.0 ($CH_3$), 22.9 ($CH_3$), 15.3 ($CH_3$).

ESMS (M+H) found=286.1, calculated for $C_{11}H_{12}IN$=285.12.

Synthesis of 5-iodo-2,3,3-trimethyl-1-(4-sulfobutyl)-3H-indol-1-ium (3)

Toluene (70 ml), 5-iodo-2,3,3-trimethyl-3H-indole (2) (12 g, 42.1 mmol) and 1,4-butane sultone (8.6 g, 63.1 mmol) were heated under reflux for 18 hrs. The reaction mixture was allowed to cool to room temperature. The resulting brown crystals were filtered and washed with acetone (3×10 ml). The filtered product was recrystallized from a solution of MeOH and diethyl ether. The crystals were collected and dried in vacuo to yield 8 g of 5-iodo-2,3,3-trimethyl-1-(4-sulfobutyl)-3H-indol-1-ium (3).

$^1H$ NMR (dmso-$d_6$): 8.27 (s, 1H, Ar—CH), 7.95 (s, 1H, Ar—CH), 7.82 (s, 1H, Ar—CH), 4.42 (brs, 2H, $CH_2$), 2.79 (s, 3H, $CH_3$), 2.47 (brs, 2H, $CH_2$), 1.90 (brs, 2H, $CH_2$), 1.69 (brs, 2H, $CH_2$), 1.49 (s, 6H, $CH_3$ X 2).

$^{13}C$ NMR (DMSO-$d_6$): 176.2, 148.4, 139.9, 136.7, 132.5, 126.8, 96.8, 49.8, 46.8, 42.6, 26.8, 25.6, 10.5.

ESMS (M+H) found=422.10, calculated for $C_{15}H_{21}INO_3S^+$=422.30.

Synthesis of 2-((E)-2-((E)-2-chloro-3-((E)-2-(5-iodo-3,3-dimethyl-1-(4-sulfobutyl) indolin-2-ylidene)ethylidene)cyclohex-1-en-1-yl) vinyl)-5-iodo-3,3-dimethyl-1-(4-sulfobutyl)-3H-indol-1-ium (5)

A solution of 3 (0.2 g, 0.47 mmol), 4 (prepared according to the method described in Flanagan et al., Bioconjugate Chem, 1997, 8, 751-756) (0.153 g, 0.47 mmol) and anhydrous sodium acetate (0.077 g, 0.93 mmol) in absolute EtOH (10 ml) under $N_2$ atmosphere was heated under reflux for 4 hr. The EtOH was removed under reduced pressure and the residue was purified by column chromatography (silica 60-120 mesh) using 25% MeOH—$CHCl_3$ mixture as eluting agent. The product (0.152 g, 33% yield) was isolated as greenish powder.

$^1H$ NMR (MeOH-$d_4$): 8.26 (d, J=7.8 Hz, 1H, Ar—CH), 8.03-7.98 (m, 2H, Ar—CH), 7.68-7.63 (m, 2H, Ar—CH), 7.63-7.49 (m, 1H, Ar—CH), 6.39-6.36 (m, 2H, CH X 2), 4.34-4.33 (m, 2H, CH X 2), 3.33-3.34 (m, 4H, $CH_2$ X 2), 2.92-2.90 (m, 2H, $CH_2$), 2.89-2.80 (m, 2H, $CH_2$), 2.08-1.96 (m, 26H, $CH_2$ X 7, $CH_3$ X 4).

$^{13}C$ NMR (DMSO-$d_6$): 174.7, 173.9, 150.1, 149.6, 148.0, 146.7, 145.9, 130.8, 134.8, 132.6, 130.1, 129.8, 128.3, 126.4, 124.7, 120.7, 116.1, 114.9, 104.6, 102.8, 98.6, 62.1, 60.1, 50:4, 29.1, 48.7, 30.5, 28.4, 28.5, 26.3, 26.2, 24.6.

ESMS (M−H+) found=977.2, calculated for $C_{38}H_{46}ClI_2N_2O_6S_2^+$=979.06.

Example 12-Diiodo-IR-820 Synthesis ($I_4$—IR783 or "I4-IRCYDYE")

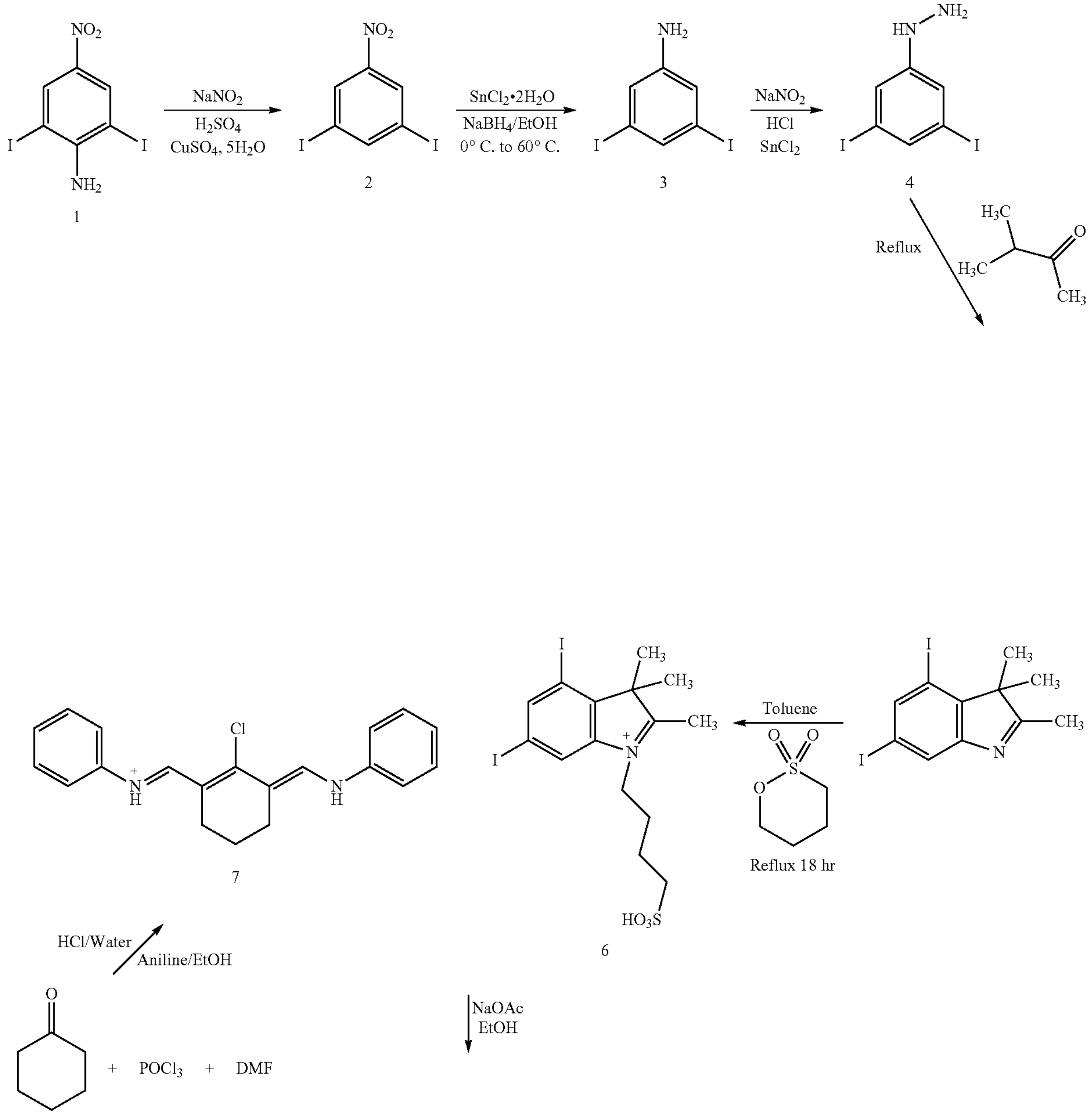

-continued

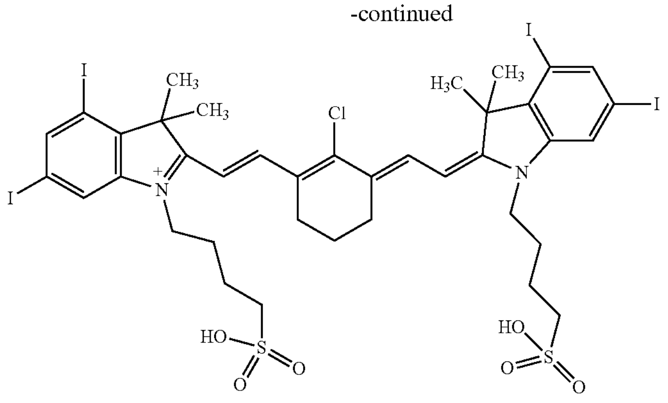

8

Synthesis of 3,5-diiodonitrobenzene (2)

To concentrated $H_2SO_4$ (96%, 15 mL) solution cooled at 0° C. was added 2,6-diiodo 4-nitroaniline 1 (3.9 g, 10 mmol) in small portions. This solution was stirred 20 minutes at this temperature and $NaNO_2$ (1.5 g, 22 mmol) was added. Stirring was continued at 0° C. for 2 h. Then, the viscous solution was poured into ice (100 g) and any solid material was filtered off. The yellow filtrate was carefully poured into a refluxed solution of $CuSO_4 \cdot 5H_2O$ (160 mg, 1 mmol) in EtOH (200 mL) and stirred for 2 h to reduce the diazonium salt. After cooling to room temperature, solid 3,5-diiodonitrobenzene (2) was separated. The product was filtered off and washed with water until neutral. The product was recrystallized from EtOH to give 2.48 g (66% yield) of fine brown needles.

$^1H$ NMR (CDCl3) δ=8.43 (t, J=1.4 Hz, 2H, Ar—CH X2), 8.29 (s, 1H, Ar—CH);

$^{13}C$ NMR (CDCl3) δ=94.1, 131.7, 148.4, 151.0.

ESMS [$M+H^+$]: calculated for $C_6H_3I_2NO_2Na$ 397.8, found 398.9 m/z.

Synthesis of 3,5-diiodoaniline (3)

To a suspension of 2 (7.15 g, 19 mmol) in anhydrous EtOH (75 mL) under argon atmosphere was added $SnCl_2 \cdot 2H_2O$ (21.6 g, 96 mmol). This mixture was brought to boil and a solution of $NaBH_4$ (361 mg, 9.5 mmol) in EtOH (40 mL) was added dropwise. The reaction mixture was stirred at reflux for 45 min. After the reaction was cooled down to 0° C., water (60 mL) was added and the mixture was neutralized with NaOH (2.5 M in $H_2O$). The aniline derivative was extracted with diethyl ether, dried over $Na_2SO_4$ and evaporated under reduced pressure to afford aniline 3 (5.86 g, 89% crude yield).

$^1H$ NMR (CDCl3) δ=7.39 (s, 1H, Ar—CH), 6.97 (s, 2H, Ar—CH X 2), 3.66 (brs, 2H, $NH_2$).

$^{13}C$ NMR (CDCl3) δ=148.5, 134.8, 122.9, 95.1.

ESMS [$M+H^+$]: calculated for $C_6H_5I_2N$ 344.8, found 345.5 m/z.

Synthesis of 3,5-diiodophenylhydrazine (4)

This compound was synthesised according to the procedure described in US 2013/0231604.

Synthesis of 4,6-diiodo-2,3,3-trimethyl-3H-indole (5)

This compound was synthesised according to the procedure described in US 2013/0231604.

Synthesis of 4,6-diiodo-2,3,3-trimethyl-1-(4-sulfobutyl)-3H-indol-1-ium (6)

Toluene (10 ml), 4,6-diiodo-2,3,3-trimethyl-3H-indole (5) (2.1 g, 5.1 mmol) and 1,4-butane sultone (3.5 g, 25.7 mmol) were heated under reflux for 18 hrs. The reaction mixture was allowed to cool to room temperature. The resulting brown crystals were filtered and washed with acetone (3×10 ml). The filtered product was recrystallized from a solution of MeOH and diethyl ether. The crystals were collected and dried in vacuo to yield 1.9 g of 4,6-diiodo-2,3,3-trimethyl-1-(4-sulfobutyl)-3H-indol-1-ium (6).

$^1H$ NMR (MeOH-$d_4$): 8.42 (s, 1H, Ar—CH), 8.36 (s, 1H, Ar—CH), 4.51-4.48 (m, 2H, $CH_2$), 2.88-2.85 (m, 2H, $CH_2$), 2.09-2.00 (m, 2H, $CH_2$), 1.99-1.82 (m, 2H, $CH_2$), 1.73 (s, 6H, $CH_3$ X 2), 1.16 (s, 3H, $CH_3$).

ESMS [$M-H^+$]: calculated for $C_{15}H_{20}I_2NO_3S^+$ 547.9, found 546.1 m/z.

Synthesis of 2-((E)-2-((E)-2-chloro-3-((E)-2-(4,6-diiodo-3,3-dimethyl-1-(4-sulfobutyl) indolin-2-ylidene)ethylidene)cyclohex-1-en-1-yl) vinyl)-4,6-diiodo-3,3-dimethyl-1-(4-sulfobutyl)-3H-indol-1-ium (8)

A solution of 8 (0.84 g, 1.5 mmol), 7 (prepared according to the method described in Flanagan et al., Bioconjugate Chem, 1997, 8, 751-756) (0.25 g, 0.7 mmol) and anhydrous sodium acetate (0.13 g, 1.5 mmol) in absolute EtOH (10 ml) under $N_2$ atmosphere was heated under reflux for 4 hr. The EtOH was removed under reduced pressure and the residue was purified by column chromatography (silica 60-120 mesh) using 25% MeOH—$CHCl_3$ mixture as eluting agent. The product (0.153 g, 8% yield) was isolated as brown powder.

$^1H$ NMR (MeOH-$d_4$): 8.59 (s, 2H, Ar—CH X 2), 8.29 (s, 2H, Ar—CH X 2), 6.77-6.75 (m, 2H, CH X 2), 5.30 (brs, 2H, CH X 2), 4.82-4.72 (m, 4H, $CH_2$ X 2), 3.39 (brs, 4H, $CH_2$ X 2), 2.60-2.47 (m, 14H, $CH_2$ X 7), 2.23 (s, 12H, $CH_3$ X 4).

$^{13}C$ NMR (DMSO-$d_6$): 170.2, 169.9, 158.9, 150.1, 149.7, 148.6, 146.8, 144.9, 140.8, 139.3, 134.2, 132.1, 126.7, 124.3, 104.0, 100.4, 96.7, 96.2, 94.5, 64.1, 59.5, 50.5, 48.7, 48.1, 30.3, 28.7, 28.2, 26.3, 26.1, 24.3.

ESMS [M−$H^+$]: calculated for $C_{38}H_{44}CI_4N_2$ $O_6S_2Na^+$ 1253.85, found 1252.81 m/z.

Example 13—In Vivo PDT Effect of $I_2$—IR783 in Mice Bearing Human Xenograft Ectopic BxPc-3 Pancreatic Cancer Tumours BxPc-3 cells were maintained in RPMI-160 medium supplemented with 10% foetal calf serum. Cells were cultured at 37° C. under 5% $CO_2$ in air. BxPc-3 cells ($1\times10^6$) were re-suspended in 100 μl of matrigel and implanted into the rear dorsal of male SCID mice. Tumour formation occurred approximately 2 weeks after implantation and tumour measurements were taken every day using callipers. Once the tumours had reached an average volume of 267 $mm^3$ calculated from the geometric mean diameter using the equation tumour volume=$4\pi R^3/3$, animals were randomly distributed into 2 groups (n=2). Following induction of anaesthesia (intraperitoneal injection of Hypnorm/Hypnovel), the treatment group received a 100 μl aliquot of $I_2$—IR783 (1 mg/kg) in a PBS: DMSO (98:2) vehicle injected directly into each tumour and treated with 780 nm light irradiation (100 mW) for 3×3 min with a 1 minute lag in between treatments. The second group (control) received vehicle only. After treatment animals were allowed to recover from anaesthesia and tumour volume was monitored at the indicated times. The % increase in tumour volume was calculated employing the pre-treatment measurements for each group. At day 8 the treatment group received a second treatment as described above but also received an intrahumoral injection of 100 μl of $O_2$MBs ($1\times10^8$ MB/mL) before light irradiation. Results are shown in FIG. 13.

Example 14—Fluorescence of 12 and 14 Analogues of IR783 ("I2-IRCYDYE" and "I4-IRCYDYE")

FIG. 14 shows (a) the UV-Vis and (b) fluorescence emission spectra of I2-IRCYDYE and I4-IRCYDYE in comparison to cardio green. The new compounds clearly show similar absorption profiles to Cardio Green. However, while the fluorescence emission of I2-IRCYDYE remains similar to cardiogreen the emission from I4-IRCYDYE is considerably quenched. This is attributed to increased ISC due to the additional iodine atoms.

Example 15—Singlet Oxygen Production and In Vitro Cytotoxicity of I2 and I4 Analogues of IR783 ("I2-IRCYDYE" and "I4-IRCYDYE")

FIG. 15 shows that both I2-IRCYDYE and I4-IRCYDYE produce more singlet oxygen than Cardio Green when excited at 780 nm.

FIG. 16 shows that both I2-IRCYDYE and I4-IRCYDYE are significantly more cytotoxic to two different pancreatic cancer cell lines (Mia Paca and BxPC-3) than cardio green when exposed to 780 nm irradiation. The compounds also proved more toxic to a cervical cancer cell line (HeLa) than Cardio Green when excited at 780 nm. In vivo experiments in mice using ectopic BxPC-3 pancreatic tumors have also shown that I2-IRCYDYE localises in tumor 18 hours following tail vein administration.

These results evidence that both I2-IRCYDYE and I4-IRCYDYE are effective NIR activated sensitisers and that I2-IRCYDYE also has potential as an imaging agent given its high NIR fluorescence. This provides the potential for image guided PDT and/or SDT of solid tumors, e.g. pancreatic tumors.

Example 16—Combined Antimetabolite/Sonodynamic Therapy of Human Pancreatic Cancer MiaPaCa-2 Cells Using Rose Bengal and 5-FU Procedure:

Human primary pancreatic adenocarcinoma cell lines MIA PaCa-2 were maintained in Dulbecco's Modified Eagle's Medium and supplemented with 10% (v/v) foetal bovine serum in a humidified 5% $CO_2$ atmosphere at 37° C. The cells were plated into the wells of a 96-well plate at a concentration of $4\times10^3$ cells per well and incubated for 21 h at 37° C. in a humidified 5% $CO_2$ atmosphere. The medium was then removed and wells treated with either Rose Bengal, (3 M), 5-Fluorouracil (50 μM) or a combination of both RB (3 μM) and 5-FU (50 μM) for 3 h. The drug solutions were then removed, fresh media added and selected wells treated with ultrasound delivered using a Sonidel SP100 sonoporator (30 sec, frequency=1 MHz, ultrasound power density=3.0 $Wcm^{-2}$, duty cycle=50% with pulse repetition frequency=100 Hz). The cells were then incubated for 24 h before cell viability was determined using a MTT assay.

Results:

The results are shown in FIG. 17. The results demonstrate that SDT treatment (i.e. RB+US) reduced cell viability by 11.1% relative to RB alone (RB−US). 5FU treatment+ultrasound reduced cell viability by 5.9% more than 5FU treatment alone. Treatment with combined SDT/5FU+ultrasound (combo+US) resulted in a 21.9% reduction relative to treatment with RB/5FU-ultrasound. Surprisingly, this difference is greater than would be expected by adding the effects caused by both treatments (17%) and indicates there is synergy by combining both techniques. (n=6).

This experiment involved just the active agents. However, these are effectively the liberated species upon microbubble destruction. The results are thus expected to extend to the situation in which the active agents are delivered using the microbubble technology herein described.

Example 17—Combined Anthracycline/Sonodynamic Therapy of Human Breast Cancer MDA-MB-231 Tumours Using Oxygen Loaded Microbubble Rose Bengal and Doxorubicin Conjugates Synthesis of Biotin-Rose Bengal and Biotin-Doxorubicin:

Synthesis of Biotin-Rose Bengal has been detailed above in Example 2. Biotin-Doxorubicin (Biotin-Dox) was prepared according to Scheme 3:

Scheme 3: Synthesis scheme for the preparation of Biotin-Dox

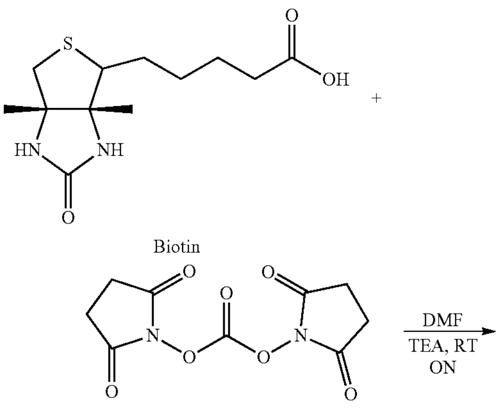

Biotin

+

Bis(2,5-dioxopyrrolin-1-yl) carbonate

-continued

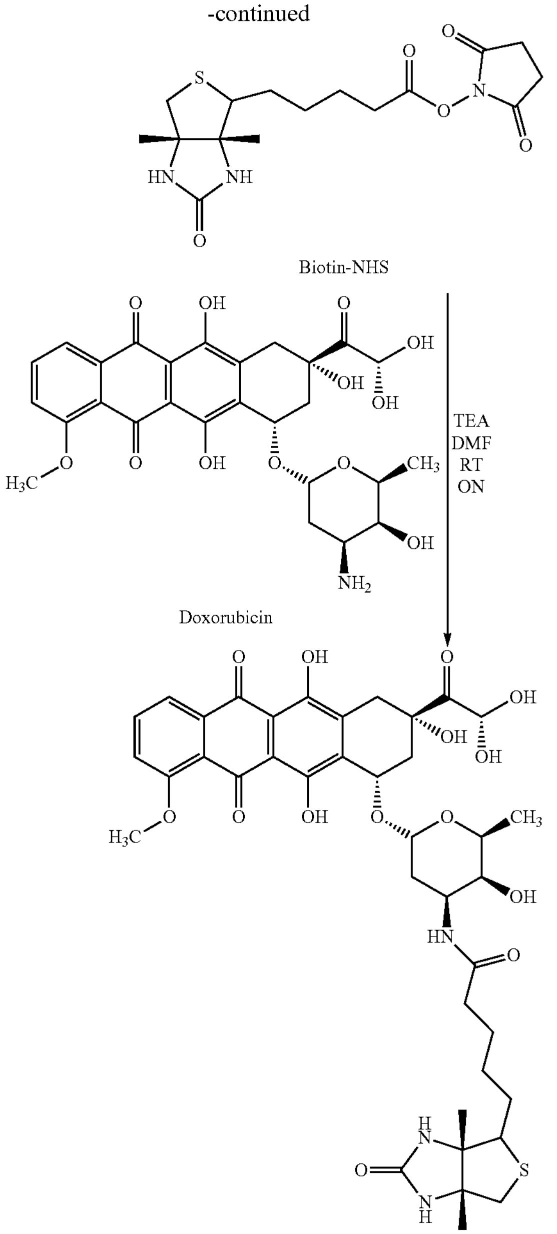

Biotin-NHS

Doxorubicin

Doxorubicin-Biotin conjugate

To an ice cold solution of biotin-N-hydroxysuccinimide ester (0.14 g, 0.41 mmol) in DMF (10 ml) was added doxorubicin (0.3 g, 0.41 mmol) under a nitrogen atmosphere. After stirring for 30 min, triethylamine (0.5 ml, 2 mmol) was added to this reaction mixture and was allowed to stir for another 12 hrs at room temperature. The reaction was monitored by TLC (Merck Silica 60, HF 254, 20:80 methanol-dichloromethane v/v). After completion of the reaction, excess diethyl ether (100 ml) was added to the reaction mixture. The red solid thus obtained was filtered and washed three times with diethyl ether (50 ml×3). This red solid was then subjected to PTLC purification using methanol-dichloromethane (20:80, v/v) as an eluent to obtain 0.25 g (Yield=78%) of biotinylated doxorubin. An analytical sample was obtained from a recrystallization of this product from ethanol.

$^1$H NMR (MeOH-$d_4$) δ: 8.54 (brs, 1H, NH), 7.82-7.76 (m, 2H, aromatic), 7.47 (d, J=7.5 Hz, 1H, aromatic), 5.39 (brs, 1H, NH), 5.05 (brs, 2H, NH, OH), 4.71 (s, 2H, —$CH_2$—OH), 4.67 (brs, 2H, OH X 2), 4.36-4.33 (m, 1H, CH), 4.25-4.22 (m, 1H, CH), 4.16-4.13 (m, 1H, CH), 3.99 (s, 3H, $OCH_3$), 3.60-3.58 (m, 1H, CH), 3.55 (brs, 2H, OH X2), 3.30-2.5 (m, 4H, $CH_2$ X1, CH X 2), 2.18-2.14 (m, 3H, $CH_2$ X 1, CH), 2.00-1.96 (m, 1H, CH), 1.63-1.50 (m, 4H, $CH_2$ X 2), 1.42-1.26 (m, 11H, $CH_3$ X 1, $CH_2$ X 4).

ESMS [M−H]: calculated for $C_{37}H_{43}I_2N_3O_{13}S$=769.25, found=767.9 m/z.

Preparation of Oxygen Loaded Microbubble Rose Bengal ($RBO_2MB$) and Doxorubicin ($DoxO_2MB$) Conjugates:

Solutions containing Biotin-RB (2.5 mg/mL) and Biotin-Dox (2.5 mg/mL) were prepared in a 0.5% DMSO solution in PBS (pH 7.4±0.1). A 2 mL aliquot of these stock solutions was then added separately to two 2 mL suspensions of avidin functionalised PFBMBs (1×10$^9$ MB/mL) and the contents vortex mixed for 15 minutes. The suspensions were then centrifuged (900 rpm) for 5 min and the MB conjugates isolated as a milky suspension floating on top of the solution. The solution was removed and replaced with a further 2 mL of stock solution containing either Biotin-RB or Biotin-Dox and the mixing/centrifugation steps repeated. The MB suspensions were then washed with PBS (5 mL), centrifuged (900 rpm) for 5 minutes and the MBs transferred to a clean centrifuge tube. This washing procedure was repeated again and the isolated PFBMB-RB and PFBMB-Dox conjugates placed in a glass vial. The PFBMB-RB and PFBMB-Dox conjugates were then sparged with oxygen gas for 2 min and the resulting $RBO_2MB$ and $DoxO_2MB$ (see FIG. 18) used directly in the animal experiments.

Treatment of Human Xenograft MDA-MB-231 Using Breast Cancer Tumors in SCID Mice:

All animals employed in this study were treated humanely and in accordance with licenced procedures under the UK Animals (Scientific Procedures) Act 1986. MDA-MB-231 cells were maintained in RPMI-1640 medium supplemented with 10% foetal calf serum as described above. Cells (1×10$^6$) were re-suspended in 100 μL of Matrigel® and implanted into the rear dorsum of female Balb/c SCID (C.B-17/IcrHan®Hsd-Prkdcscid) mice. Tumour formation occurred approximately 2 weeks after implantation and tumour measurements were taken every other day using calipers. Once the tumours had reached an average volume of 100 mm$^3$, calculated from the geometric mean diameter using the equation tumour volume=4πR$^3$/3, animals were randomly distributed into 3 groups (n=3). Following induction of anaesthesia (intraperitoneal injection of Hypnorm/Hypnovel), group 1 received 100 μL of $RBO_2MB$ (300 μM RB); group 2 received 100 μL of $DoxO_2MB$ (475 μM) and group 3 received 100 μL containing $RBO_2$ MB (150 μM RB) and of $DoxO_2MB$ (237.5 μM). Intratumoural injection was chosen as the route of administration to preclude experimental variation resulting from pharmacokinetic behaviour of the platform. The tumours were then treated with ultrasound for 3.5 min at an ultrasound frequency of 1 MHz, an ultrasound power density of 3.5 Wcm$^{-2}$ ($I_{SATP}$; spatial average temporal peak) and using a duty cycle of 30% at a pulse repetition frequency of 100 Hz. Treatments were repeated on Day 14. After treatments, animals were allowed to recover from anaesthesia and tumour volume and body weight were recorded daily for nine days. The % increase in tumour volume was calculated employing the pre-treatment measurements for each group.

Results:

The results are shown in FIG. 19. The results show that the combined $DoxO_2MB/RBO_2MB$+US treatment was more effective than $RBO_2MB$+US and as effective as $DoxO_2MB$+US using half the concentration of Doxorubicin and Rose Bengal. The results demonstrate that the platform may be employed to treat breast cancer.

The invention claimed is:

1. A method of treating cancer via sonodynamic therapy, said method comprising:

administration to cells or tissues of a patient in need thereof a microbubble-chemotherapeutic agent complex, wherein said complex is additionally attached to or associated with at least one sonosensitiser, wherein said method comprises subjecting said cells or tissues to ultrasound irradiation to rupture the microbubble and activate the sonosensitizer, and wherein said chemotherapeutic agent is a taxane and said sonosensitiser is Rose Bengal.

2. The method as claimed in claim 1, wherein the microbubble-chemotherapeutic agent complex comprises a microbubble attached to or associated with the chemotherapeutic agent, via a non-covalent linkage.

3. The method as claimed in claim 1, wherein the microbubble-chemotherapeutic agent complex comprises a microbubble having a shell which retains a gas.

4. The method as claimed in claim 1, wherein said microbubble-chemotherapeutic agent complex comprises a microbubble having a diameter of less than 200 μm.

5. The method as claimed in claim 1, wherein said microbubble-chemotherapeutic agent complex comprises a phospholipid monolayer shell having linked thereto one or more polymers.

6. A pharmaceutical composition comprising a microbubble-chemotherapeutic agent, together with at least one pharmaceutical carrier or excipient, wherein the microbubble-chemotherapeutic agent complex is additionally attached to or associated with at least one sonosensitiser, and wherein said chemotherapeutic agent is a taxane and said sonosensitiser is Rose Bengal.

7. A method of treating cancer via sonodynamic therapy, said method comprising administration to cells or tissues of a patient in need thereof a pharmaceutical composition as claimed in claim 6, and subjecting said cells or tissues to ultrasound irradiation to rupture the microbubbles and activate the sonosensitiser.

8. The method as claimed in claim 1, wherein said cancer is selected from the group consisting of sarcomas, including osteogenic and soft tissue sarcomas, carcinomas, lymphomas, including Hodgkin and non-Hodgkin lymphomas, neuroblastoma, melanoma, myeloma, Wilm's tumour, and leukemias, including acute lymphoblastic leukaemia and acute myeloblastic leukaemia, astrocytomas, gliomas and retinoblastomas.

9. The method as claimed in claim 8, wherein said cancer is pancreatic cancer.

10. A microbubble having linked thereto at least one chemotherapeutic agent and at least one sonosensitiser, wherein said chemotherapeutic agent is a taxane and said sonosensitiser is Rose Bengal.

11. The method as claimed in claim 1, wherein said complex is additionally attached to or associated with the at least one sonosensitiser via a non-covalent linkage.

12. The method as claimed in claim 11, wherein said non-covalent linkage is a biotin-avidin interaction.

13. The method as claimed in claim 2, wherein the non-covalent linkage is a biotin-avidin interaction.

14. The method as claimed in claim 3, wherein said gas is oxygen.

15. The pharmaceutical composition as claimed in claim 6, wherein said microbubble-chemotherapeutic agent complex comprises a microbubble having non-covalently bound thereto said chemotherapeutic agent and said at least one sonosensitiser.

16. The method as claimed in claim 8, wherein said cancer is selected from breast, lung, cerebral, bladder, thyroid, prostate, colon, rectum, pancreas, stomach, liver, uterine, hepatic, renal, prostate, cervical and ovarian carcinoma.

17. The method as claimed in claim 1, where the taxane is paclitaxel or docetaxel.

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 1

cctttgatgc ccatttactc ta                                              22


<210> SEQ ID NO 2
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 2

agcggctatg ttattctgga c                                               21


<210> SEQ ID NO 3
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 3

cgtgggccgc cctaggcacc a                                               21


<210> SEQ ID NO 4
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 4

ttggccttag ggttcagggg gg                                              22


<210> SEQ ID NO 5
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 5

tgactcaaca cgggaaacc                                                  19


<210> SEQ ID NO 6
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 6

tcgctccacc aactaagaac                                                 20
```